United States Patent
O'Neil et al.

(10) Patent No.: US 10,588,754 B2
(45) Date of Patent: Mar. 17, 2020

(54) LATERAL SPONDYLOLISTHESIS REDUCTION CAGE AND INSTRUMENTS AND METHODS FOR NON-PARALLEL DISC SPACE PREPARATION

(71) Applicant: DePuy Synthes Products, Inc., Raynham, MA (US)

(72) Inventors: Michael J. O'Neil, West Barnstable, MA (US); Douglas Raymond, Bridgewater, MA (US); Jonathan Bellas, Bridgewater, MA (US); Derek Shaw, North Attleboro, MA (US)

(73) Assignee: DePuy Snythes Products, Inc., Raynham, MA (US)

( * ) Notice: Subject to any disclaimer, the term of this patent is extended or adjusted under 35 U.S.C. 154(b) by 0 days.

(21) Appl. No.: 15/726,515

(22) Filed: Oct. 6, 2017

(65) Prior Publication Data

US 2018/0028200 A1    Feb. 1, 2018

Related U.S. Application Data

(60) Continuation of application No. 14/496,765, filed on Sep. 25, 2014, now Pat. No. 9,801,639, which is a (Continued)

(51) Int. Cl.
*A61M 25/00* (2006.01)
*A61M 25/01* (2006.01)
(Continued)

(52) U.S. Cl.
CPC ........ *A61F 2/4455* (2013.01); *A61B 17/1659* (2013.01); *A61B 17/1671* (2013.01); *A61B 17/1757* (2013.01); *A61F 2/30771* (2013.01); *A61F 2/446* (2013.01); *A61F 2/447* (2013.01); *A61F 2/4425* (2013.01);
(Continued)

(58) Field of Classification Search
CPC .............. A61B 17/3431; A61B 5/4893; A61B 2017/3433; A61M 25/0133
See application file for complete search history.

(56) References Cited

U.S. PATENT DOCUMENTS

| 4,105,034 A | 8/1978 | Shalaby et al. |
| 4,130,639 A | 12/1978 | Shalaby et al. |

(Continued)

FOREIGN PATENT DOCUMENTS

| DE | 197 10 392 C1 | 7/1999 |
| DE | 10357960 A1 | 7/2005 |

(Continued)

OTHER PUBLICATIONS

Allcock, "Polyphosphazenes"; The Encyclopedia of Polymer Science; 1988; pp. 31-41; vol. 13; Wiley Intersciences, John Wiley & Sons.

(Continued)

*Primary Examiner* — Ellen C Hammond
(74) *Attorney, Agent, or Firm* — Nutter McClennen & Fish LLP

(57) ABSTRACT

An intervertebral fusion device comprising inferior and superior fusion cage devices that provide an ability to correct spondylolisthesis via in-situ adjustment.

13 Claims, 25 Drawing Sheets

Related U.S. Application Data division of application No. 13/163,427, filed on Jun. 17, 2011, now Pat. No. 8,845,733, and a division of application No. 13/163,471, filed on Jun. 17, 2011, now Pat. No. 9,282,979, and a division of application No. 13/163,496, filed on Jun. 17, 2011, now Pat. No. 9,907,560, and a division of application No. 13/163,517, filed on Jun. 17, 2011, now Pat. No. 9,763,678, and a division of application No. 13/163,397, filed on Jun. 17, 2011, now Pat. No. 9,592,063.

(60) Provisional application No. 61/466,302, filed on Mar. 22, 2011, provisional application No. 61/397,716, filed on Nov. 30, 2010, provisional application No. 61/410,177, filed on Nov. 4, 2010, provisional application No. 61/385,958, filed on Sep. 23, 2010, provisional application No. 61/379,194, filed on Sep. 1, 2010, provisional application No. 61/358,220, filed on Jun. 24, 2010.

(51) Int. Cl.
*A61F 2/44* (2006.01)
*A61B 17/16* (2006.01)
*A61B 17/17* (2006.01)
*A61M 29/02* (2006.01)
*A61F 2/46* (2006.01)
*A61F 2/30* (2006.01)
*A61B 5/00* (2006.01)
*A61B 17/02* (2006.01)
*A61B 17/34* (2006.01)

(52) U.S. Cl.
CPC .......... *A61F 2/4611* (2013.01); *A61F 2/4637* (2013.01); *A61M 29/02* (2013.01); *A61B 5/4893* (2013.01); *A61B 2017/0256* (2013.01); *A61B 2017/3433* (2013.01); *A61F 2/4465* (2013.01); *A61F 2002/30326* (2013.01); *A61F 2002/30523* (2013.01); *A61F 2002/30593* (2013.01); *A61F 2002/443* (2013.01); *A61F 2002/4623* (2013.01); *A61F 2002/4642* (2013.01); *A61M 25/0054* (2013.01); *A61M 25/0133* (2013.01)

(56) References Cited

U.S. PATENT DOCUMENTS

| | | |
|---|---|---|
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,538,612 A | 9/1985 | Patrick, Jr. |
| 4,834,757 A | 5/1989 | Brantigan |
| 4,863,476 A | 9/1989 | Shepperd |
| 4,995,200 A | 2/1991 | Eberhart |
| 5,006,121 A | 4/1991 | Hafeli |
| 5,019,082 A | 5/1991 | Frey et al. |
| 5,123,926 A | 6/1992 | Pisharodi |
| 5,133,719 A | 7/1992 | Winston |
| 5,163,939 A | 11/1992 | Winston |
| 5,169,402 A | 12/1992 | Elloy |
| 5,171,278 A | 12/1992 | Pisharodi |
| 5,217,475 A | 6/1993 | Kuber |
| 5,250,061 A | 10/1993 | Michelson |
| 5,320,644 A | 6/1994 | Baumgartner |
| 5,342,365 A | 8/1994 | Waldman |
| 5,387,215 A | 2/1995 | Fisher |
| 5,390,683 A | 2/1995 | Pisharodi |
| 5,454,815 A | 10/1995 | Geisser et al. |
| 5,454,827 A | 10/1995 | Aust et al. |
| 5,464,929 A | 11/1995 | Bezwada et al. |
| 5,522,899 A | 6/1996 | Michelson |
| 5,540,693 A | 7/1996 | Fisher |
| 5,554,191 A | 9/1996 | Lahille |
| 5,595,751 A | 1/1997 | Bezwada et al. |
| 5,597,579 A | 1/1997 | Bezwada et al. |
| 5,601,561 A | 2/1997 | Terry et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,645,850 A | 7/1997 | Bezwada et al. |
| 5,648,088 A | 7/1997 | Bezwada et al. |
| 5,658,335 A | 8/1997 | Allen |
| 5,665,122 A | 9/1997 | Kambin |
| 5,693,100 A | 12/1997 | Pisharodi |
| 5,698,213 A | 12/1997 | Jamiolkowski et al. |
| 5,700,583 A | 12/1997 | Jamiolkowski et al. |
| 5,725,531 A | 3/1998 | Shapiro |
| 5,857,995 A | 1/1999 | Thomas et al. |
| 5,859,150 A | 1/1999 | Jamiolkowski et al. |
| 5,865,848 A | 2/1999 | Baker |
| 5,916,228 A | 6/1999 | Ripich et al. |
| 5,916,267 A | 6/1999 | Tienboon |
| 5,925,056 A | 7/1999 | Thomas et al. |
| 5,976,187 A | 11/1999 | Richelsoph |
| 5,980,522 A | 11/1999 | Koros et al. |
| 6,039,761 A | 3/2000 | Li et al. |
| 6,045,579 A | 4/2000 | Hochshuler et al. |
| 6,053,922 A | 4/2000 | Krause et al. |
| 6,056,763 A | 5/2000 | Parsons |
| 6,066,175 A | 5/2000 | Henderson et al. |
| 6,080,158 A | 6/2000 | Lin |
| 6,106,557 A | 8/2000 | Robioneck et al. |
| 6,120,508 A | 9/2000 | Grunig et al. |
| 6,126,689 A | 10/2000 | Brett |
| 6,139,558 A | 10/2000 | Wagner |
| 6,176,882 B1 | 1/2001 | Biedermann et al. |
| 6,241,733 B1 | 6/2001 | Nicholson et al. |
| 6,251,140 B1 | 6/2001 | Marino et al. |
| 6,258,093 B1 | 7/2001 | Edwards et al. |
| 6,296,644 B1 | 10/2001 | Saurat et al. |
| D450,676 S | 11/2001 | Huttner |
| 6,332,894 B1 | 12/2001 | Stalcup et al. |
| 6,342,074 B1 | 1/2002 | Simpson |
| 6,387,130 B1 | 5/2002 | Stone et al. |
| 6,398,793 B1 | 6/2002 | McGuire |
| 6,409,766 B1 | 6/2002 | Brett |
| 6,413,278 B1 | 7/2002 | Marchosky |
| 6,436,101 B1 | 8/2002 | Hamada |
| 6,447,518 B1 | 9/2002 | Krause et al. |
| 6,595,998 B2 | 7/2003 | Johnson et al. |
| 6,610,066 B2 | 8/2003 | Dinger et al. |
| 6,635,060 B2 | 10/2003 | Hanson et al. |
| RE38,335 E | 11/2003 | Aust et al. |
| 6,641,582 B1 | 11/2003 | Hanson et al. |
| 6,660,004 B2 | 12/2003 | Barker et al. |
| 6,733,535 B2 | 5/2004 | Michelson |
| 6,755,837 B2 | 6/2004 | Ebner |
| 6,764,491 B2 | 7/2004 | Frey |
| 6,835,208 B2 | 12/2004 | Marchosky |
| 6,840,941 B2 | 1/2005 | Rogers et al. |
| 6,878,167 B2 | 4/2005 | Ferree |
| 6,949,108 B2 | 9/2005 | Holmes |
| 6,966,912 B2 | 11/2005 | Michelson |
| 7,018,415 B1 | 3/2006 | McKay |
| 7,060,073 B2 | 6/2006 | Frey et al. |
| 7,070,598 B2 | 7/2006 | Lim et al. |
| 7,087,055 B2 | 8/2006 | Lim et al. |
| 7,125,424 B2 | 10/2006 | Banick et al. |
| 7,226,482 B2 | 6/2007 | Messerli et al. |
| 7,326,248 B2 | 2/2008 | Michelson |
| 7,351,262 B2 | 4/2008 | Bindseil et al. |
| 7,470,273 B2 | 12/2008 | Dougherty-Shah |
| 7,491,237 B2 | 2/2009 | Randall et al. |
| 7,503,920 B2 | 3/2009 | Siegal |
| 7,572,279 B2 | 8/2009 | Jackson |
| 7,575,580 B2 | 8/2009 | Lim et al. |
| 7,578,820 B2 | 8/2009 | Moore et al. |
| 7,601,173 B2 | 10/2009 | Messerli et al. |
| 7,618,458 B2 | 11/2009 | Biedermann et al. |

(56) References Cited

U.S. PATENT DOCUMENTS

| | | |
|---|---|---|
| 7,625,377 B2 | 12/2009 | Veldhuizen et al. |
| 7,625,394 B2 | 12/2009 | Molz, IV et al. |
| 7,655,010 B2 | 2/2010 | Serhan et al. |
| 7,666,186 B2 | 2/2010 | Harp |
| 7,666,226 B2 | 2/2010 | Schaller |
| 7,670,374 B2 | 3/2010 | Schaller |
| 7,674,265 B2 | 3/2010 | Smith et al. |
| 7,682,400 B2 | 3/2010 | Zwirkoski |
| 7,703,727 B2 | 4/2010 | Selness |
| 7,704,280 B2 | 4/2010 | Lechmann et al. |
| 7,731,751 B2 | 6/2010 | Butler et al. |
| 7,763,028 B2 | 7/2010 | Lim et al. |
| 7,763,038 B2 | 7/2010 | O'Brien |
| 7,771,473 B2 | 8/2010 | Thramann |
| 7,785,368 B2 | 8/2010 | Schaller |
| 7,799,081 B2 | 9/2010 | McKinley |
| 7,803,161 B2 | 9/2010 | Foley et al. |
| 7,828,849 B2 | 11/2010 | Lim |
| 7,837,734 B2 | 11/2010 | Zucherman et al. |
| 7,850,733 B2 | 12/2010 | Baynham et al. |
| 7,918,874 B2 | 4/2011 | Siegal |
| 7,922,719 B2 | 4/2011 | Ralph et al. |
| 7,938,857 B2 | 5/2011 | Garcia-Bengochea et al. |
| 7,942,903 B2 | 5/2011 | Moskowitz et al. |
| 7,963,967 B1 | 6/2011 | Woods |
| 8,007,535 B2 | 8/2011 | Hudgins et al. |
| 8,012,212 B2 | 9/2011 | Link et al. |
| 8,025,697 B2 | 9/2011 | McClellan, III et al. |
| 8,034,110 B2 | 10/2011 | Garner et al. |
| 8,038,703 B2 | 10/2011 | Dobak, III et al. |
| 8,043,293 B2 | 10/2011 | Warnick |
| 8,057,544 B2 | 11/2011 | Schaller |
| 8,105,382 B2 | 1/2012 | Olmos et al. |
| 8,128,700 B2 | 3/2012 | Delurio et al. |
| 8,206,423 B2 | 6/2012 | Siegal |
| 8,216,317 B2 | 7/2012 | Thibodeau |
| 8,241,364 B2 | 8/2012 | Hansell et al. |
| 8,262,666 B2 | 9/2012 | Baynham et al. |
| 8,267,939 B2 | 9/2012 | Cipoletti et al. |
| 8,343,193 B2 | 1/2013 | Johnson et al. |
| 8,343,222 B2 | 1/2013 | Cope |
| 8,366,777 B2 | 2/2013 | Matthis et al. |
| 8,382,842 B2 | 2/2013 | Greenhalgh et al. |
| 8,403,990 B2 | 3/2013 | Dryer et al. |
| 8,454,617 B2 | 6/2013 | Schaller et al. |
| 8,579,981 B2 | 11/2013 | Lim et al. |
| 8,628,577 B1 | 1/2014 | Jimenez |
| 8,663,331 B2 | 3/2014 | McClellan, III et al. |
| 8,845,733 B2 | 9/2014 | O'Neil et al. |
| 8,845,734 B2 | 9/2014 | Weiman |
| 8,920,506 B2 | 12/2014 | McGuckin, Jr. |
| 8,926,704 B2 | 1/2015 | Glerum et al. |
| 8,940,050 B2 | 1/2015 | Laurence et al. |
| 8,961,609 B2 | 2/2015 | Schaller |
| 8,968,408 B2 | 3/2015 | Schaller et al. |
| 9,101,488 B2 | 8/2015 | Malandain |
| 9,101,492 B2 | 8/2015 | Mangione et al. |
| 9,282,979 B2* | 3/2016 | O'Neil .............. A61B 17/1671 |
| 9,801,639 B2 | 10/2017 | O'Neil et al. |
| 9,801,640 B2 | 10/2017 | O'Neil et al. |
| 2002/0138078 A1 | 9/2002 | Chappuis |
| 2002/0143399 A1 | 10/2002 | Sutcliffe |
| 2002/0165535 A1* | 11/2002 | Lesh .................. A61B 17/2202 606/41 |
| 2002/0165550 A1 | 11/2002 | Frey |
| 2002/0183758 A1 | 12/2002 | Middleton et al. |
| 2002/0198521 A1* | 12/2002 | Maguire ............ A61B 18/1492 606/41 |
| 2003/0028251 A1 | 2/2003 | Mathews |
| 2003/0135275 A1 | 7/2003 | Garcia et al. |
| 2003/0139812 A1 | 7/2003 | Garcia et al. |
| 2003/0191531 A1 | 10/2003 | Berry et al. |
| 2004/0002761 A1 | 1/2004 | Rogers et al. |
| 2004/0030387 A1 | 2/2004 | Landry et al. |
| 2004/0059337 A1 | 3/2004 | Hanson et al. |
| 2004/0068269 A1 | 4/2004 | Bonati et al. |
| 2004/0083000 A1 | 4/2004 | Keller et al. |
| 2004/0087947 A1 | 5/2004 | Lim et al. |
| 2004/0102784 A1 | 5/2004 | Pasquet et al. |
| 2004/0102846 A1 | 5/2004 | Keller et al. |
| 2004/0127990 A1 | 7/2004 | Bartish, Jr. et al. |
| 2004/0147129 A1 | 7/2004 | Rolfson |
| 2004/0220668 A1 | 11/2004 | Eisermann et al. |
| 2005/0038431 A1 | 2/2005 | Bartish et al. |
| 2005/0096745 A1 | 5/2005 | Andre et al. |
| 2005/0119752 A1 | 6/2005 | Williams et al. |
| 2005/0149034 A1 | 7/2005 | Assell et al. |
| 2005/0165420 A1 | 7/2005 | Cha |
| 2005/0165484 A1 | 7/2005 | Ferree |
| 2005/0171541 A1 | 8/2005 | Boehm et al. |
| 2005/0177173 A1 | 8/2005 | Aebi et al. |
| 2005/0240193 A1 | 10/2005 | Layne et al. |
| 2005/0261683 A1 | 11/2005 | Veldhuizen et al. |
| 2005/0267463 A1* | 12/2005 | Vanney .............. A61B 18/1492 606/41 |
| 2006/0036244 A1 | 2/2006 | Spitler et al. |
| 2006/0058807 A1 | 3/2006 | Landry et al. |
| 2006/0064101 A1 | 3/2006 | Arramon |
| 2006/0064102 A1 | 3/2006 | Ebner |
| 2006/0069436 A1 | 3/2006 | Sutton et al. |
| 2006/0074429 A1 | 4/2006 | Ralph et al. |
| 2006/0100622 A1 | 5/2006 | Jackson |
| 2006/0111715 A1 | 5/2006 | Jackson |
| 2006/0111728 A1 | 5/2006 | Abdou |
| 2006/0122701 A1 | 6/2006 | Kiester |
| 2006/0129244 A1 | 6/2006 | Ensign |
| 2006/0142858 A1 | 6/2006 | Colleran et al. |
| 2006/0167547 A1 | 7/2006 | Suddaby |
| 2006/0189999 A1 | 8/2006 | Zwirkoski |
| 2006/0212118 A1 | 9/2006 | Abernathie |
| 2006/0229627 A1 | 10/2006 | Hunt et al. |
| 2006/0229724 A1 | 10/2006 | Lechmann et al. |
| 2006/0235426 A1 | 10/2006 | Lim et al. |
| 2006/0253120 A1 | 11/2006 | Anderson et al. |
| 2006/0254784 A1 | 11/2006 | Hartmann et al. |
| 2006/0265077 A1 | 11/2006 | Zwirkoski |
| 2006/0276902 A1 | 12/2006 | Zipnick et al. |
| 2006/0293753 A1 | 12/2006 | Thramann |
| 2007/0055264 A1 | 3/2007 | Parmigiani |
| 2007/0055272 A1 | 3/2007 | Schaller |
| 2007/0067035 A1 | 3/2007 | Falahee |
| 2007/0093897 A1 | 4/2007 | Gerbec et al. |
| 2007/0093901 A1 | 4/2007 | Grotz et al. |
| 2007/0142843 A1 | 6/2007 | Dye |
| 2007/0162132 A1 | 7/2007 | Messerli |
| 2007/0213737 A1 | 9/2007 | Schermerhorn et al. |
| 2007/0213826 A1 | 9/2007 | Smith et al. |
| 2007/0225726 A1 | 9/2007 | Dye et al. |
| 2007/0225815 A1 | 9/2007 | Keith et al. |
| 2007/0233130 A1 | 10/2007 | Suddaby |
| 2007/0250167 A1 | 10/2007 | Bray et al. |
| 2007/0260314 A1 | 11/2007 | Biyani |
| 2007/0270957 A1 | 11/2007 | Heinz |
| 2007/0270968 A1 | 11/2007 | Baynham et al. |
| 2008/0027544 A1 | 1/2008 | Melkent |
| 2008/0027550 A1 | 1/2008 | Link et al. |
| 2008/0045966 A1 | 2/2008 | Buttermann et al. |
| 2008/0051890 A1 | 2/2008 | Waugh et al. |
| 2008/0058933 A1 | 3/2008 | Garner et al. |
| 2008/0065082 A1 | 3/2008 | Chang et al. |
| 2008/0077150 A1 | 3/2008 | Nguyen |
| 2008/0077241 A1 | 3/2008 | Nguyen |
| 2008/0082173 A1 | 4/2008 | Delurio et al. |
| 2008/0091211 A1 | 4/2008 | Gately |
| 2008/0097454 A1 | 4/2008 | DeRidder et al. |
| 2008/0108990 A1 | 5/2008 | Mitchell et al. |
| 2008/0119935 A1 | 5/2008 | Alvarez |
| 2008/0125865 A1 | 5/2008 | Abdelgany |
| 2008/0133012 A1 | 6/2008 | McGuckin |
| 2008/0140085 A1 | 6/2008 | Gately et al. |
| 2008/0154379 A1 | 6/2008 | Steiner et al. |
| 2008/0172128 A1 | 7/2008 | Perez-Cruet et al. |
| 2008/0208255 A1 | 8/2008 | Siegal |
| 2008/0221586 A1 | 9/2008 | Garcia-Bengochea et al. |

(56) References Cited

U.S. PATENT DOCUMENTS

| | | |
|---|---|---|
| 2008/0221687 A1 | 9/2008 | Viker |
| 2008/0234732 A1 | 9/2008 | Landry et al. |
| 2008/0234733 A1 | 9/2008 | Scrantz et al. |
| 2008/0243126 A1 | 10/2008 | Gutierrez et al. |
| 2008/0243255 A1 | 10/2008 | Butler et al. |
| 2008/0249628 A1 | 10/2008 | Altarac et al. |
| 2008/0255563 A1 | 10/2008 | Farr et al. |
| 2008/0255574 A1 | 10/2008 | Dye |
| 2008/0269904 A1 | 10/2008 | Voorhies |
| 2008/0312743 A1 | 12/2008 | Vila et al. |
| 2009/0030423 A1 | 1/2009 | Puno |
| 2009/0054898 A1 | 2/2009 | Gleason |
| 2009/0054911 A1 | 2/2009 | Mueller et al. |
| 2009/0062807 A1 | 3/2009 | Song |
| 2009/0076607 A1 | 3/2009 | Aalsma et al. |
| 2009/0088789 A1 | 4/2009 | O'Neil et al. |
| 2009/0112217 A1 | 4/2009 | Hester |
| 2009/0143859 A1 | 6/2009 | McClellan, III et al. |
| 2009/0164016 A1 | 6/2009 | Georgy et al. |
| 2009/0182431 A1 | 7/2009 | Butler et al. |
| 2009/0192616 A1 | 7/2009 | Zielinski |
| 2009/0216234 A1 | 8/2009 | Farr et al. |
| 2009/0221967 A1* | 9/2009 | Thommen .......... A61B 17/22031 604/164.09 |
| 2009/0234364 A1 | 9/2009 | Crook |
| 2009/0240335 A1 | 9/2009 | Arcenio et al. |
| 2009/0276049 A1 | 11/2009 | Weiland |
| 2009/0299479 A1 | 12/2009 | Jones et al. |
| 2010/0016968 A1 | 1/2010 | Moore |
| 2010/0030217 A1 | 2/2010 | Mitusina |
| 2010/0076502 A1* | 3/2010 | Guyer .................... A61B 17/02 606/86 R |
| 2010/0094422 A1 | 4/2010 | Hansell et al. |
| 2010/0100098 A1 | 4/2010 | Norton et al. |
| 2010/0100183 A1* | 4/2010 | Prewett .............. A61B 17/7065 623/17.11 |
| 2010/0125334 A1 | 5/2010 | Krueger |
| 2010/0161060 A1 | 6/2010 | Schaller et al. |
| 2010/0174321 A1 | 7/2010 | Schaller |
| 2010/0185290 A1 | 7/2010 | Compton et al. |
| 2010/0191241 A1 | 7/2010 | McCormack et al. |
| 2010/0198263 A1 | 8/2010 | Siegal et al. |
| 2010/0211076 A1 | 8/2010 | Germain et al. |
| 2010/0211107 A1 | 8/2010 | Muhanna |
| 2010/0217269 A1 | 8/2010 | Landes |
| 2010/0234849 A2 | 9/2010 | Bouadi |
| 2010/0249935 A1 | 9/2010 | Slivka et al. |
| 2010/0256768 A1 | 10/2010 | Lim et al. |
| 2010/0274358 A1 | 10/2010 | Mueller et al. |
| 2010/0280619 A1 | 11/2010 | Yuan et al. |
| 2010/0305700 A1 | 12/2010 | Ben-Arye et al. |
| 2010/0305704 A1 | 12/2010 | Messerli et al. |
| 2010/0331845 A1 | 12/2010 | Foley et al. |
| 2011/0004216 A1 | 1/2011 | Amendola et al. |
| 2011/0009970 A1 | 1/2011 | Puno |
| 2011/0029083 A1 | 2/2011 | Hynes et al. |
| 2011/0029085 A1 | 2/2011 | Hynes et al. |
| 2011/0035011 A1 | 2/2011 | Cain |
| 2011/0106260 A1 | 5/2011 | Laurence et al. |
| 2011/0112586 A1 | 5/2011 | Guyer et al. |
| 2011/0125266 A1 | 5/2011 | Rodgers et al. |
| 2011/0190891 A1 | 8/2011 | Suh et al. |
| 2011/0276142 A1 | 11/2011 | Niemiec et al. |
| 2011/0282459 A1 | 11/2011 | McClellan, III et al. |
| 2011/0301712 A1 | 12/2011 | Palmatier et al. |
| 2011/0319898 A1* | 12/2011 | O'Neil ................ A61B 17/1671 606/84 |
| 2011/0319899 A1 | 12/2011 | O'Neil et al. |
| 2011/0319998 A1 | 12/2011 | O'Neil et al. |
| 2011/0319999 A1 | 12/2011 | O'Neil et al. |
| 2011/0320000 A1 | 12/2011 | O'Neil et al. |
| 2012/0035730 A1 | 2/2012 | Spann |
| 2012/0165943 A1 | 6/2012 | Mangione et al. |
| 2012/0209383 A1 | 8/2012 | Tsuang et al. |
| 2012/0277877 A1 | 11/2012 | Smith et al. |
| 2012/0310352 A1 | 12/2012 | DiMauro et al. |
| 2013/0006362 A1 | 1/2013 | Biedermann et al. |
| 2013/0023937 A1 | 1/2013 | Biedermann et al. |
| 2013/0035762 A1 | 2/2013 | Siegal et al. |
| 2013/0079790 A1 | 3/2013 | Stein et al. |
| 2013/0109925 A1 | 5/2013 | Horton et al. |
| 2013/0110239 A1 | 5/2013 | Siegal et al. |
| 2013/0116791 A1 | 5/2013 | Theofilos |
| 2013/0138214 A1 | 5/2013 | Greenhalgh et al. |
| 2013/0150906 A1 | 6/2013 | Kerboul et al. |
| 2013/0173004 A1 | 7/2013 | Greenhalgh et al. |
| 2013/0190875 A1 | 7/2013 | Shulock et al. |
| 2013/0238006 A1 | 9/2013 | O'Neil et al. |
| 2013/0268077 A1 | 10/2013 | You et al. |
| 2013/0310937 A1 | 11/2013 | Pimenta |
| 2014/0025170 A1 | 1/2014 | Lim et al. |
| 2014/0039626 A1 | 2/2014 | Mitchell |
| 2014/0052259 A1 | 2/2014 | Garner et al. |
| 2014/0058512 A1 | 2/2014 | Petersheim |
| 2014/0058513 A1 | 2/2014 | Gahman et al. |
| 2014/0172103 A1 | 6/2014 | O'Neil et al. |
| 2014/0172105 A1 | 6/2014 | Frasier et al. |
| 2015/0032212 A1 | 1/2015 | O'Neil et al. |
| 2015/0094812 A1 | 4/2015 | Cain |
| 2015/0196400 A1 | 7/2015 | Dace |
| 2016/0038306 A1 | 2/2016 | O'Neil et al. |
| 2017/0128231 A1 | 5/2017 | O'Neil et al. |
| 2018/0036141 A1 | 2/2018 | O'Neil et al. |

FOREIGN PATENT DOCUMENTS

| | | |
|---|---|---|
| EP | 609084 A2 | 8/1994 |
| EP | 1283026 A2 | 2/2003 |
| EP | 1308132 A2 | 5/2003 |
| EP | 1405602 A1 | 4/2004 |
| EP | 1605836 A1 | 12/2005 |
| EP | 1829486 A1 | 9/2007 |
| FR | 2 874 814 A1 | 3/2006 |
| FR | 2948277 A1 | 1/2011 |
| JP | 2006-501901 A | 1/2006 |
| WO | 92/014423 A1 | 9/1992 |
| WO | 98/034568 A1 | 8/1998 |
| WO | 99/060956 A1 | 12/1999 |
| WO | 99/063914 A1 | 12/1999 |
| WO | 00/24343 A1 | 5/2000 |
| WO | 00/74605 A1 | 12/2000 |
| WO | 2002/003870 A1 | 1/2002 |
| WO | 2003/003951 A1 | 1/2003 |
| WO | 2004/030582 A2 | 4/2004 |
| WO | 2004/069033 A2 | 8/2004 |
| WO | 2004/080316 A1 | 9/2004 |
| WO | 2005/094297 A2 | 10/2005 |
| WO | 2006/044920 A2 | 4/2006 |
| WO | 2006/072941 A2 | 7/2006 |
| WO | 2006/118944 A1 | 11/2006 |
| WO | 2007/048012 A2 | 4/2007 |
| WO | 2008/005627 A2 | 1/2008 |
| WO | 2010/011348 A1 | 1/2010 |
| WO | 2010/075555 A2 | 7/2010 |
| WO | 2010/121002 A1 | 10/2010 |
| WO | 2011/013047 A2 | 2/2011 |
| WO | 2011/060087 A1 | 5/2011 |
| WO | 2012/027490 A2 | 3/2012 |
| WO | 2012/103254 A2 | 8/2012 |
| WO | 2012/129197 A1 | 9/2012 |
| WO | 2013/149611 A1 | 10/2013 |

OTHER PUBLICATIONS

Cohn, "Biodegradable PEO/PLA Block Copolymers"; Journal of Biomedical Materials Research; 1988; pp. 993-1009; vol. 22; John Wiley & Sons, Inc.

Cohn, "Polymer Preprints"; Journal of Biomaterials Research; 1989; p. 498; Biomaterials Research Laboratory, Casali Institute of Applied Chemistry, Israel.

Heller, "Poly (Ortho Esters)"; Handbook of Biodegradable Polymers; edited by Domb; et al; Hardwood Academic Press; 1997; pp. 99-118.

(56) References Cited

OTHER PUBLICATIONS

Japanese Office Action for Application No. 2013-542047, dated Sep. 8, 2015 (12 pages).
Japanese Office Action for Application No. 2016-135826, dated Jun. 6, 2017 (7 pages).
Kemnitzer, "Degradable Polymers Derived From the Amino Acid L-Tyrosine"; 1997; pp. 251-272; edited by Domb, et al., Hardwood Academic Press.
Khoo, Axilif address spondy from the caudal approach. Minimally Invasive Correction of Grade I and II Isthmic Spondylolisthesis using AxiaLiF for L5/S1 Fusion, pp. 45-0123 Rev B Sep. 15, 2008.
U.S. Appl. No. 61/178,315, filed May 14, 2009.
Vandorpe, "Biodegradable Polyphosphazenes for Biomedical Applications"; Handbook of Biodegradable Polymers; 1997; pp. 161-182; Hardwood Academic Press.
U.S. Appl. No. 13/163,397, filed Jun. 17, 2011, Universal Trial for Lateral Cages.
U.S. Appl. No. 13/163,427, filed Jun. 17, 2011, Lateral Spondylolisthesis Reduction Cage.
U.S. Appl. No. 13/163,471, filed Jun. 17, 2011, Instruments and Methods for Non-Parallel Disc Space Preparation.
U.S. Appl. No. 13/163,496, filed Jun. 17, 2011, Flexible Vertebral Body Shavers.
U.S. Appl. No. 13/163,517, filed Jun. 17, 2011, Multi-Segment Lateral Cage Adapted to Flex Substantially in the Coronal Plane.
U.S. Appl. No. 14/496,765, filed Sep. 25, 2014, Lateral Spondylolisthesis Reduction Cage.
U.S. Appl. No. 14/919,863, filed Oct. 22, 2015, Lateral Spondylolisthesis Reduction Cage.
U.S. Appl. No. 15/415,299, filed Jan. 25, 2017, Lateral Spondylolisthesis Reduction Cage.
U.S. Appl. No. 15/788,178, filed Oct. 19, 2017, Lateral Spondylolisthesis Reduction Cage.

\* cited by examiner

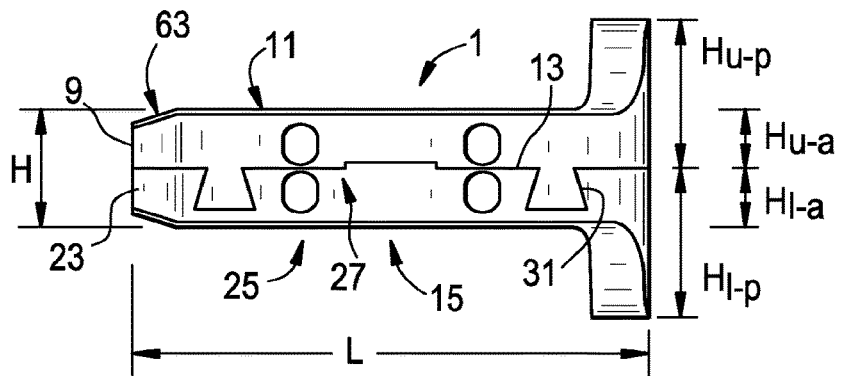
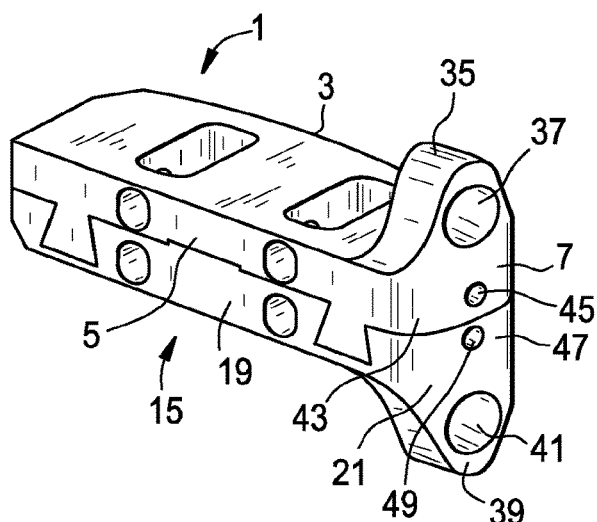
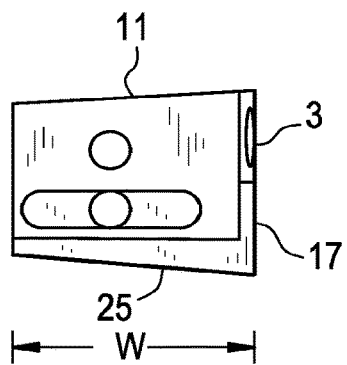
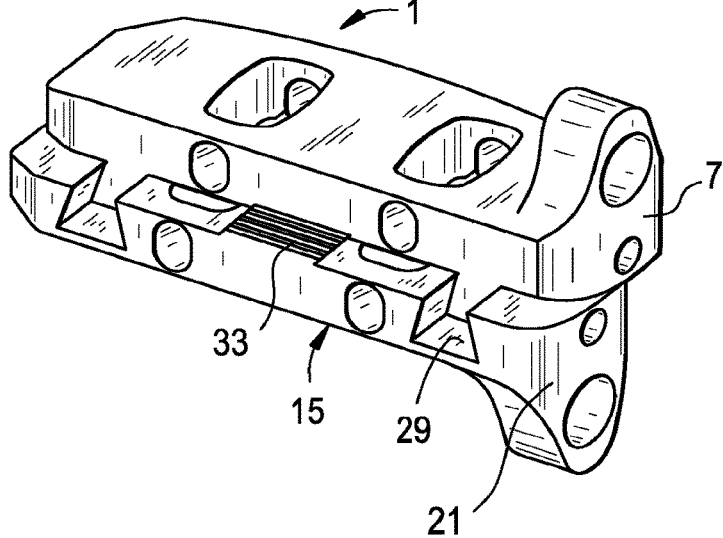

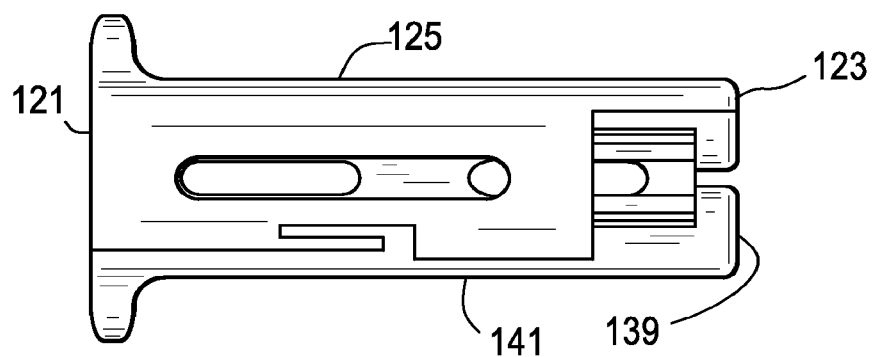
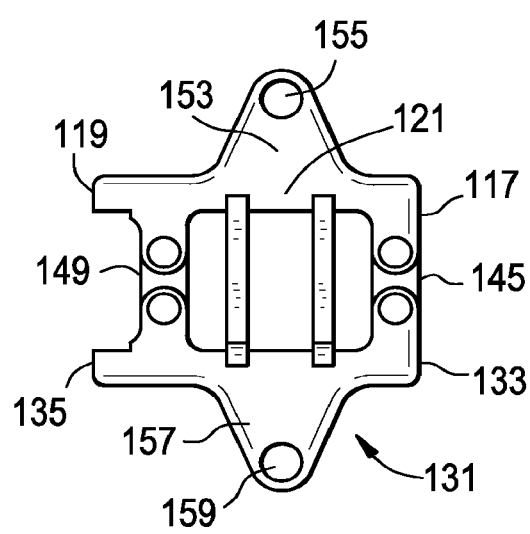
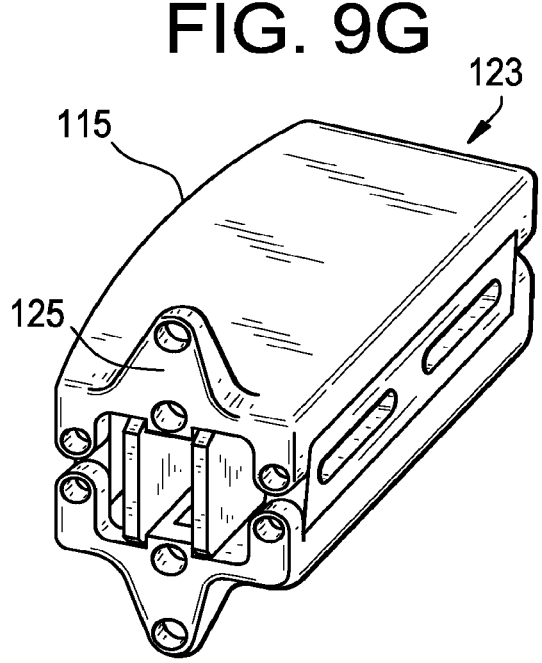

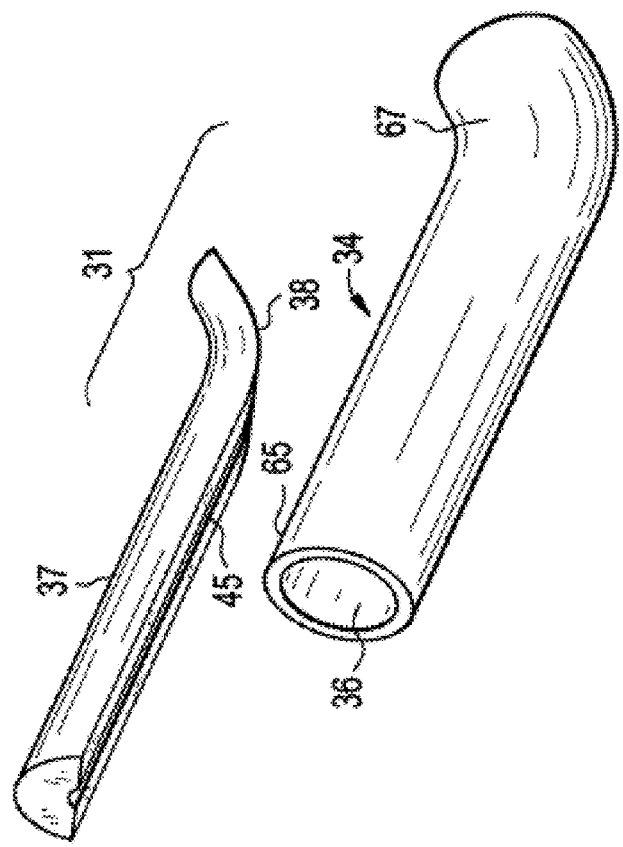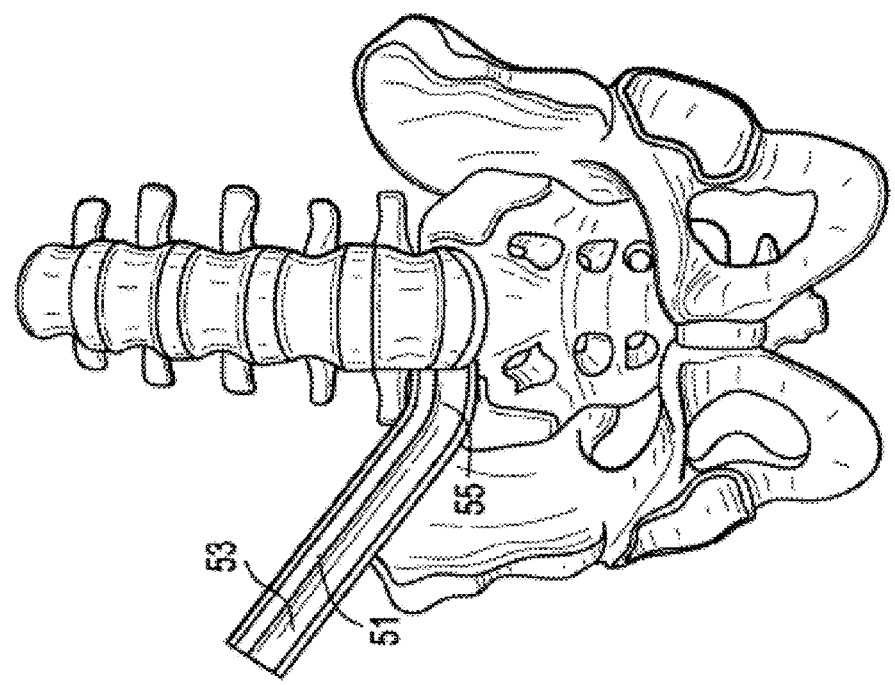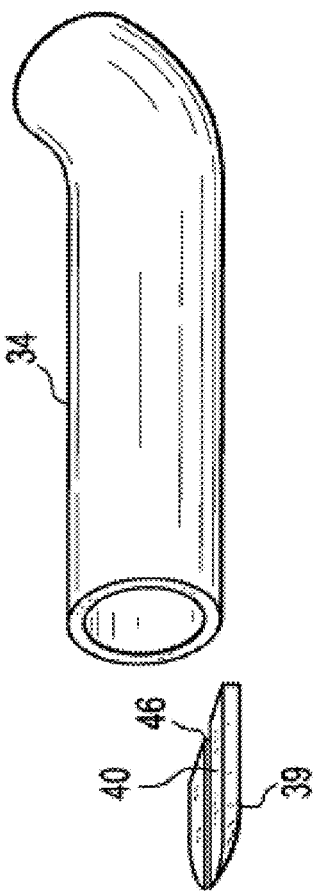

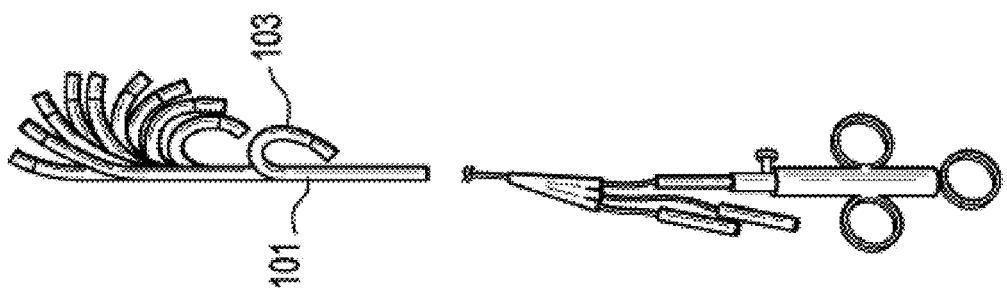
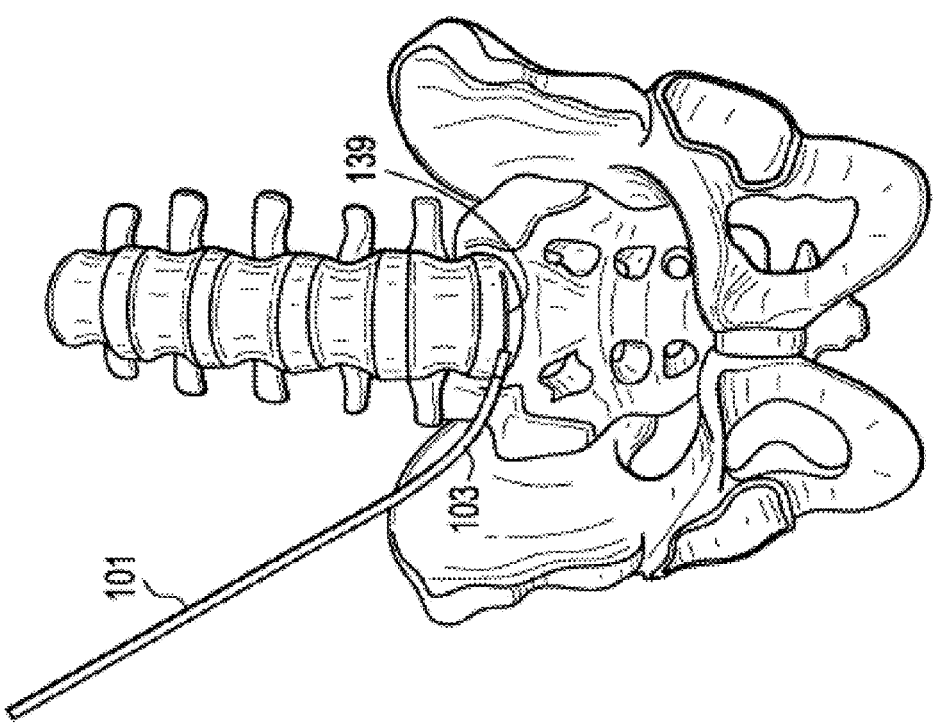
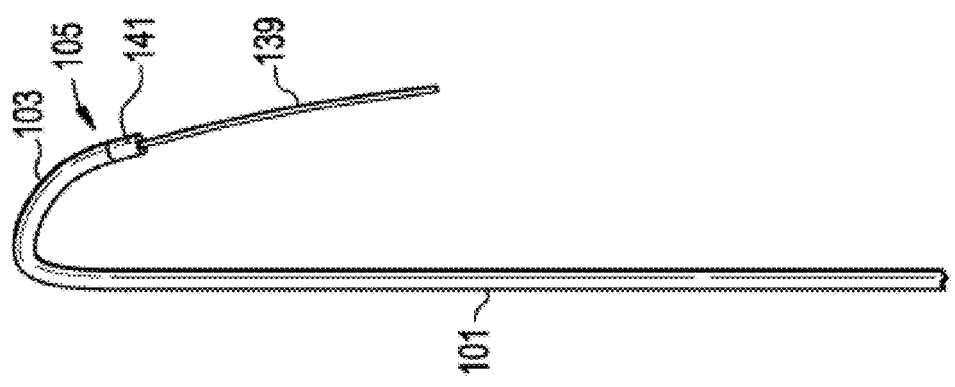

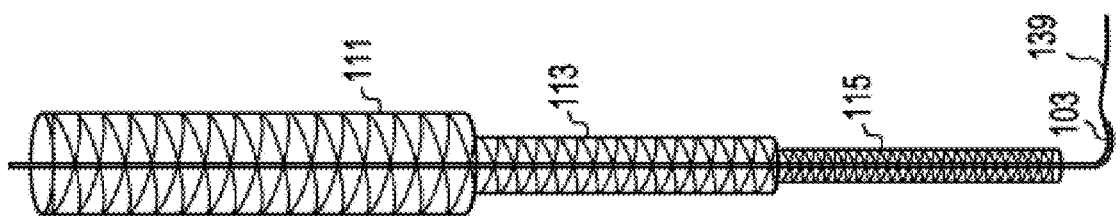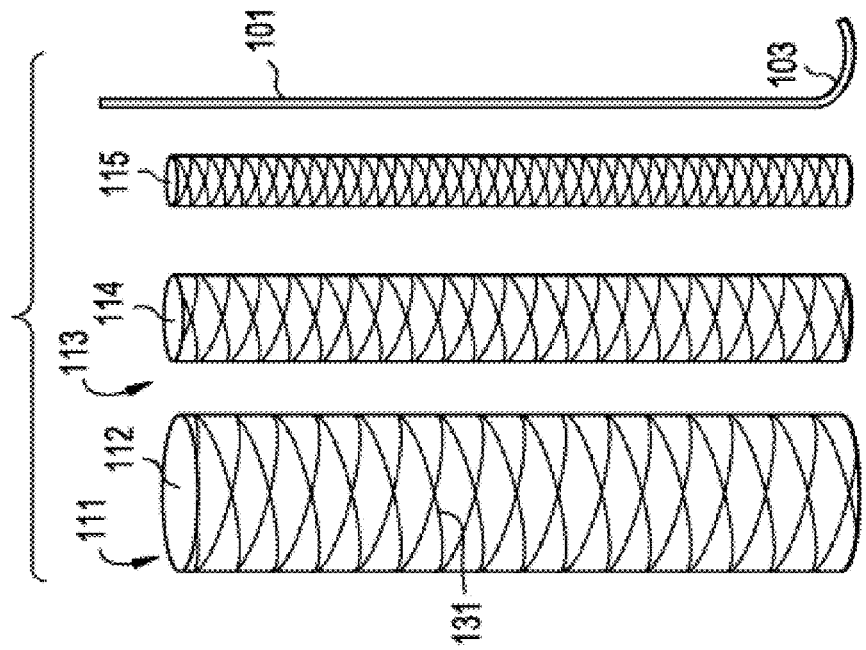

LATERAL SPONDYLOLISTHESIS REDUCTION CAGE AND INSTRUMENTS AND METHODS FOR NON-PARALLEL DISC SPACE PREPARATION

CONTINUING DATA

This application is a continuation of patent application U.S. Ser. No. 14/496,765, filed Sep. 25, 2014, entitled "Lateral Spondylolisthesis Reduction Cage", referred to below as "the '765 application," which is incorporated by reference in its entirety.

The '765 application is a division of patent application U.S. Ser. No. 13/163,427, filed Jun. 17, 2011 (now U.S. Pat. No. 8,845,733), entitled "Lateral Spondylolisthesis Reduction Cage" which claims priority to provisional application U.S. Ser. No. 61/466,302 filed Mar. 22, 2011; provisional application U.S. Ser. No. 61/397,716 filed Nov. 30, 2010; provisional application U.S. Ser. No. 61/410,177 filed Nov. 4, 2010; provisional application U.S. Ser. No. 61/385,958, filed Sep. 23, 2010; provisional application U.S. Ser. No. 61/379,194 filed Sep. 1, 2010; and provisional application U.S. Ser. No. 61/358,220 filed Jun. 24, 2010, all of which are incorporated by reference in their entireties.

The '765 application is a division of patent application U.S. Ser. No. 13/163,471, filed Jun. 17, 2011 (now U.S. Pat. No. 9,282,979), entitled "Instruments and Methods for Non-Parallel Disc Space Preparation" which claims priority to provisional application U.S. Ser. No. 61/466,302 filed Mar. 22, 2011; provisional application U.S. Ser. No. 61/397,716 filed Nov. 30, 2010; provisional application U.S. Ser. No. 61/410,177 filed Nov. 4, 2010; provisional application U.S. Ser. No. 61/385,958, filed Sep. 23, 2010; provisional application U.S. Ser. No. 61/379,194 filed Sep. 1, 2010; and provisional application U.S. Ser. No. 61/358,220 filed Jun. 24, 2010, all of which are incorporated by reference in their entireties.

The '765 application is a division of patent application U.S. Ser. No. 13/163,496, filed Jun. 17, 2011, entitled "Flexible Vertebral Body Shavers", which claims priority to provisional application U.S. Ser. No. 61/466,302 filed Mar. 22, 2011; provisional application U.S. Ser. No. 61/397,716 filed Nov. 30, 2010; provisional application U.S. Ser. No. 61/410,177 filed Nov. 4, 2010; provisional application U.S. Ser. No. 61/385,958, filed Sep. 23, 2010; provisional application U.S. Ser. No. 61/379,194 filed Sep. 1, 2010; and provisional application U.S. Ser. No. 61/358,220 filed Jun. 24, 2010, all of which are incorporated by reference in their entireties.

The '765 application is a division of patent application U.S. Ser. No. 13/163,517, filed Jun. 17, 2011 (now U.S. Pat. No. 9,763,678), entitled "Multi-Segment Lateral Cages adapted to Flex Substantially in the Coronal Plane", which claims priority to provisional application U.S. Ser. No. 61/466,302 filed Mar. 22, 2011; provisional application U.S. Ser. No. 61/397,716 filed Nov. 30, 2010; provisional application U.S. Ser. No. 61/410,177 filed Nov. 4, 2010; provisional application U.S. Ser. No. 61/385,958, filed Sep. 23, 2010; provisional application U.S. Ser. No. 61/379,194 filed Sep. 1, 2010; and provisional application U.S. Ser. No. 61/358,220 filed Jun. 24, 2010, all of which are incorporated by reference in their entireties.

The '765 application is a division of patent application U.S. Ser. No. 13/163,397, filed Jun. 17, 2011 (now U.S. Pat. No. 9,592,063), entitled "Universal Trial for Lateral Cages", which claims priority to provisional application U.S. Ser. No. 61/466,302 filed Mar. 22, 2011; provisional application U.S. Ser. No. 61/397,716 filed Nov. 30, 2010; provisional application U.S. Ser. No. 61/410,177 filed Nov. 4, 2010; provisional application U.S. Ser. No. 61/385,958, filed Sep. 23, 2010; provisional application U.S. Ser. No. 61/379,194 filed Sep. 1, 2010; and provisional application U.S. Ser. No. 61/358,220 filed Jun. 24, 2010, all of which are incorporated by reference in their entireties.

BACKGROUND OF THE INVENTION

Lateral interbody fusion procedures are currently indicated for patients with ≤grade 1 spondylolisthesis. However, correction from the lateral approach is currently limited to regaining height and lordosis with only a low degree of spondylolisthesis correction, as the straight or lordotic cage is impacted during insertion to expand the disc space. Significant spondylolisthesis reduction is currently accomplished via a posterior approach with supplemental posterior fixation devices, including facet screws, translaminar screws, pedicle screws and rods, as well as intraspinous process devices or plates.

Although current lateral cages are characterized by symmetric superior and inferior geometries, the normal and degenerated discs do not have such similar superior and inferior endplate geometries. The lack of conformity of the cage endplate to the pertinent vertebral body can promote cage malpositioning during insertion, improper load balancing, increased settling and/or subsidence, as well as device movement following implantation.

Some surgeons using lateral cages attach lateral plating to the cage to achieve enhanced cage securement accompanied by some degree of biomechanical stabilization. However, most currently available lateral cages do not provide for plate attachment.

US 2004-0220668 (Eisermann) discloses a method for correcting spondylolisthesis from the lateral approach is provided in which a pair of insertion members are inserted laterally into upper and lower vertebrae, a connecting member is affixed to the insertion members, and a rotating force is applied to the connecting member to encourage the upper and lower vertebrae into a desired position relative to one another. In FIG. 9-11 of Eisermann, in an alternative embodiment, a slidable prosthetic joint can be used to help with the lateral approach for treating spondylolisthesis. The sliding joint extends generally along the longitudinal axis and includes a first slidable component and a second slidable component. The slidable components cooperate to form the sliding joint which is sized and configured for disposition within an intervertebral space between adjacent vertebral bodies. The sliding joint provides movement between the adjacent vertebral bodies to maintain or restore some of the motion similar to the normal bio-mechanical motion provided by a natural intervertebral disc. More specifically, the slidable components are permitted to translate relative to one another in the axial plane.

US Patent Publication No. 2010-0016968 (Moore) discloses an apparatus and method that allow for the realignment and stabilization of adjacent vertebrae. An implant of this invention both repositions adjacent vertebrae and remains in situ to maintain the new position. The implant has two halves which are interlocked such that they can slide horizontally with respect to each other. Movement of the implant halves and their respective positions are controlled by external set screw and internal locking block within the implant. The implant includes radial anchors which fit into alignment slots made in the misaligned vertebra by the disclosed method. The set screws are used to advance the halves of the implant which in turn move the misaligned vertebrae back into correct positions. The correct position of the vertebrae is locked in place through a bolt and a plate.

U.S. Pat. No. 6,342,074 (Simpson) discloses a spinal fusion implant and method for maintaining proper lumbar spine curvature and intervertebral disc spacing where a degenerative disc has been removed. The one-piece implant comprises a hollow body having an access passage for insertion of bone graft material into the intervertebral space after the implant has been affixed to adjacent vertebrae. The implant provides a pair of screw-receiving passages that are oppositely inclined relative to a central plane. In one embodiment, the screw-receiving passages enable the head of an orthopedic screw to be retained entirely within the access passage. A spinal fusion implant embodied in the present invention may be inserted anteriorally or laterally. FIG. 4 discloses a device having fixtures for attaching to a lateral side of a vertebral body.

U.S. Pat. No. 6,878,167 (Ferree) discloses an osteotomy of a portion of a vertebral endplate and/or vertebral body allowing for easier insertion of a device that fits tightly into a disc space. It also discloses a mechanical device to hold the osteotomized portion of the vertebra against the vertebral body after the intradiscal device is placed. The device may be removed after the pieces of vertebra heal and fuse together. It further discloses a device secured to a side of the vertebral body in FIG. 4C.

The lateral access approach is frequently utilized to deliver interbody fusion cages to the lumbar spine. In comparison to conventional anterior or posterior approaches to the lumbar spine, the lateral approach is thought to minimize posterior and/or anterior tissue damage as well as reduce surgery time, associated blood loss, and infection risk.

When multi-level access to the spine is provided through a single minimal access port, the insertion trajectory to the superior and inferior levels is not parallel to those levels. In addition, direct lateral access parallel to the L4/5 and L5/S1 levels is prevented by the presence of the iliac crest.

Accordingly, the angled trajectory required for lateral access to these lower levels requires the cages to be implanted at a "malpositioned" angle that prevents balanced loading across the vertebral endplates and spine. See FIG. 1. This "malpositioned" access, associated endplate damage and device placement can initiate subsidence and spinal instability.

Current spreader and shaver technology includes varying paddle shapes and cutting geometries with rigid drive shafts. US Patent Publication No. 2008-00445966 discloses a chisel cutting guide for excising a portion of a vertebral body.

Conventional dilation systems used in intervertebral fusion procedures are typically rigid and non-steerable. Accordingly, they require a line of sight insertion towards the target disc.

US Patent Publication No. US 2007-0225815 (Annulex) discloses a curved stylet for steering within a disc space Annulex does not disclose an assembly comprising a curved guide wire and a flexible dilator tube.

SUMMARY OF THE INVENTION

The present invention relates to an intervertebral fusion device comprising inferior and superior fusion cages that provide an ability to correct spondylolisthesis via lateral insertion and in-situ adjustment.

Therefore, in accordance with the present invention, there is provided an intervertebral fusion device for correcting spondylolisthesis in a patient, comprising:

a) an upper cage having an anterior wall, a posterior wall, and a proximal wall and a distal wall connecting the anterior and posterior walls, and an upper surface for contacting an upper vertebral body and a lower surface, b) a lower cage having an anterior wall, a posterior wall, and a proximal wall and a distal wall connecting the anterior and posterior walls, and a lower surface for contacting a lower vertebral body and an upper surface, wherein the lower surface of the upper cage slidingly mates with upper surface of the lower cage.

Also in accordance with the present invention, there is provided a method for correcting spondylolisthesis in a patient, comprising the steps of:

a) selecting a fusion device comprising an upper cage and a lower cage, b) fixing the upper cage to an upper vertebral body of the patient and the lower cage to a lower vertebral body of the patient, and c) moving the upper cage relative to the lower cage to correct the spondylolisthesis.

Also in accordance with the present invention, there is provided an intervertebral fusion device for correcting spondylolisthesis in a patient, comprising:

a) an upper cage having an anterior wall, a posterior wall, and a proximal wall and a distal wall connecting the anterior and posterior walls, and an upper surface for contacting an upper vertebral body and a lower surface having a first groove therein, b) a lower cage having an anterior wall, a posterior wall, and a proximal wall and a distal wall connecting the anterior and posterior walls, and a lower surface for contacting a lower vertebral body and an upper surface having a second groove therein, and c) a locking plate, wherein the lower surface of the upper cage contacts the upper surface of the lower cage so that the first and second grooves form a first throughhole running from the proximal wall to about the distal wall. wherein the locking plate is disposed in the first throughhole.

Also in accordance with the present invention, there is provided an intervertebral fusion device for correcting spondylolisthesis in a patient, comprising:

a) an upper cage having an anterior wall, a posterior wall, and a proximal wall and a distal wall connecting the anterior and posterior walls, and an upper surface for contacting an upper vertebral body and a lower surface, b) a lower cage having an anterior wall, a posterior wall, and a proximal wall and a distal wall connecting the anterior and posterior walls, and a lower surface for contacting a lower vertebral body and an upper surface, wherein the anterior wall is connected to the proximal wall by a first dual linkage and to the distal wall by a second dual linkage, wherein the posterior wall is connected to the proximal wall by a third dual linkage and to the distal wall by a fourth dual linkage. wherein the linkages allow the upper plate to pivot relative to the lower plate in the plane of the proximal wall.

Also in accordance with the present invention, there is provided an intervertebral fusion device for correcting spondylolisthesis in a patient, comprising:

a) an upper wall having an upper surface adapted for contacting an upper vertebral body and an inner surface, b) a lower wall having a lower surface adapted for contacting a lower vertebral body and an inner surface, c) proximal and distal walls extending between the upper and lower walls, d) anterior and posterior walls extending between the upper and lower walls, e) a rack-and-pinion mechanism located between the inner surfaces of the upper and lower walls wherein the pinion extends substantially from the distal wall to the proximal wall, wherein the rack extends substantially from the anterior wall to the posterior wall, so that rotation of the pinion effects relative movement of the upper and lower walls in the anterior-posterior direction.

The present inventors have developed flexible shavers and curved access ports that reduce the above-mentioned access and trajectory problems associated with conventional lateral approaches to the lower spine. The devices and methods of the present invention allow the surgeon to present disc preparation instruments to a disc space in the lower spine in a manner that is parallel to the disc space. Consequently, these devices and methods allow for preparing with less endplate damage and higher preparation symmetry.

Therefore, in accordance with the present invention there is provided a flexible shaver for preparing a vertebral endplate, comprising:

a) a shaft having a proximal end portion and a distal end portion, b) a handle attached to the proximal end portion of the shaft, and c) a shaving head attached to the distal end portion of the shaft, the head comprising:

i) an body portion;

ii) a first face forming a first cutting edge, and wherein the shaft and head comprise a universal joint.

Also in accordance with the present invention there is provided a method of intervertebral disc space preparation, comprising the steps of:

a) selecting a shaver having a flexible shaft;

b) inserting the shaver into an intervertebral disc space bounded by opposed vertebral endplates, and c) contacting the shaver to a vertebral endplate.

Also in accordance with the present invention there is provided a method of preparing an intervertebral disc space between opposing vertebral endplates, comprising the steps of:

a) inserting a curved (preferably flexible) port into a lateral aspect of the disc space, the curved port having a bore.

Also in accordance with the present invention there is provided a assembly comprising:

a) a curved port having a bore having a transverse cross-section; and b) a vertebral endplate shaver having a transverse cross-section, wherein the shaver is disposed within the bore of the curved port, wherein the transverse cross-section of the bore substantially corresponds to the transverse cross-section of the shaver so as to determine the orientation of the shaver within the bore.

Also in accordance with the present invention there is provided a port for use in preparing an intervertebral disc space, comprising:

a) an outer cannula having a bore, and b) an inner cannula having a bore having a non-circular transverse cross-section, wherein the inner cannula is disposed within the bore of the outer cannula.

Also in accordance with the present invention there is provided a port for use in preparing an intervertebral disc space, the port comprising a longitudinal bore therethrough, the bore having a proximal end portion having a transverse cross-section and a distal end portion having a transverse cross-section, wherein the transverse cross-section of the proximal end portion of the bore is greater than that transverse cross-section of the distal end portion of the bore.

Also in accordance with the present invention there is provided a port for use in preparing an intervertebral disc space, comprising:

a) an outer cannula having a bore having a proximal end portion and a distal end portion, b) an upper insert disposed at least in the distal end portion of the bore, and c) a lower insert disposed at least in the distal end portion of the bore.

Also in accordance with the present invention there is provided a assembly for providing access to an intervertebral disc, comprising;

a) a catheter having a steerable tip, b) a first flexible dilator tube having a first bore defining a first longitudinal axis, c) a second flexible dilator tube having a second bore defining a second longitudinal axis, wherein the first flexible dilator tube is received with the bore of the second flexible dilator tube, and wherein the steerable tip is received within the bore of the first flexible dilator tube.

Also in accordance with the present invention there is provided a method of accessing a target intervertebral disc, comprising the steps of:

a) advancing a steerable catheter having a tip through an incision and towards the target disc, b) imparting a first curve in the tip of the steerable catheter, c) docking the curved tip upon the target disc, d) advancing a first flexible dilator tube over the curved tip to impart a first curve in the first flexible dilator tube.

The present invention also relates to an assembly comprising a steerable, curvable guide wire and a set of flexible dilator tubes having sequentially increasing bore diameters. When a flexible dilator tube is passed over the curved guide wire, the flexible dilator tube curves in an arc substantially similar to that of the curved guide wire. Thus, the set of curved dilator tubes can open up a curved access path to the L4/5 and L5/S1 levels that previously could not be directly accessed due to the presence of the iliac crest.

Also in accordance with the present invention there is provided a flexible shaver for preparing a vertebral endplate, comprising:

a) a shaft having a proximal end portion and a distal end portion, b) a handle attached to the proximal end portion of the shaft, and c) a shaving head attached to the distal end portion of the shaft, the head comprising:

i) an body portion;

ii) a first face forming a first cutting edge, and wherein the shaft comprises a flexible portion.

Also in accordance with the present invention there is provided a method of performing a procedure on a spine, comprising the step of:

a) advancing an instrument along a curved path, the path being substantially in a coronal plane, towards a lateral aspect of an intervertebral disc.

DESCRIPTION OF THE DRAWINGS

FIGS. 4a-4d show various views of the intervertebral fusion device of the present invention.

FIGS. 9a-9g disclose various views of a dual linkage embodiment of the present invention.

FIG. 19A presents an exploded version of a port of the present invention comprising an outer cannula and an upper insert.

FIG. 19B presents an assembled version of a port of the present invention comprising an outer cannula and an upper and lower insert.

FIG. 19C presents the port of FIG. A-6B laterally docked onto the lower spine.

FIG. 22A discloses a steerable catheter having a guide wire extending therefrom.

FIG. 22B discloses the steerable catheter of FIG. 22A docked onto a spine.

FIG. 22C discloses a steerable catheter displaying various degrees of curved tips.

FIG. 23A discloses three flexible dilation tubes and a steerable catheter.

FIG. 23B discloses an assembly of three flexible dilation tubes and a steerable catheter.

DETAILED DESCRIPTION OF THE INVENTION

Figure 1:
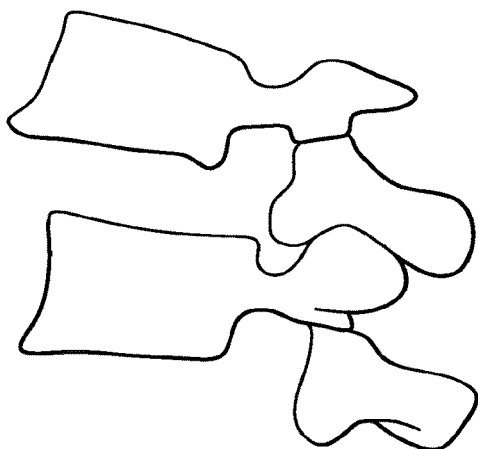
FIG. 1 is a side view of a functional spinal unit having grade 1 spondylolisthesis characterized by a 20-25% slip.

FIG. 1 is a side view of a functional spinal unit having grade 1 spondylolisthesis characterized by a 20-25% slip.

In use, the devices of the present invention accomplish improved and controlled spondylolisthesis correction with fusion from the lateral approach. The lateral cage devices of the present invention also provide for intra-operative trialing and selection to enhance conformance of the cage geometry to the vertebral body endplates bounding the targeted disc space. The fusion device of the present invention provides for direct attachment of its superior and inferior cages to the lateral aspects of the opposing vertebral bodies.

Several devices and methods for correcting spondylolisthesis with fusion from the lateral approach are disclosed. All incorporate a superior and inferior fusion cages that are fixedly attached to the corresponding vertebral bodies. The fixed attachment can be accomplished by using pre-attached plates, or by incorporating internal screws (e.g., the STALIF approach) and/or lateral keels. Following implantation, the superior and inferior cages are aligned in-situ via various activation means that are further discussed below, and then locked in place.

The interior, contacting surfaces of the cages that effect intra-device attachment contain alignment and securement features that allow for controlled intra-operative manipulation of the spine in the sagittal plane following individual fixed attachment of the cages to the superior and inferior vertebral bodies. These features can include but are not limited to teeth, barbs, and dovetails.

Both the superior and inferior cages can include features on their outer surfaces that can enhance securement to the vertebral body endplate. These features include fins, barbs, teeth, osteoconductive surface morphology (porosity) and coatings (such as HA and TCP). The superior and inferior cages can also include graft-retention windows and pockets to facilitate the long-term fusion of the two vertebral bodies of the functional spinal unit.

The inner contacting surfaces of the cage can be flat to allow for the incremental lineal adjustment of the relative cage positions. Alternatively, these surfaces can be domed so as to enable the accurate adjustment of the vertebral bodies to a centered position in the flexion/extension plane (i.e., to the center of rotation).

The external geometry of the superior and inferior cages can be flat or lordotic, and can be domed or angled in various plans to enhance their conformance to the vertebral body endplates and to address spinal deformity and/or scoliosis.

Figure 2A:
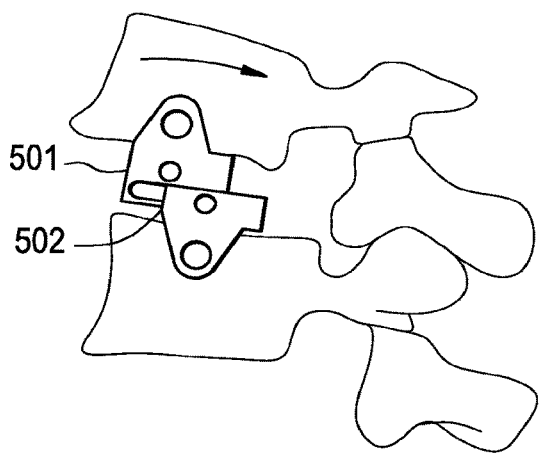
FIGS. 2a-2b and 3 disclose the implantation of the fusion device of the present invention, in which the cages of the device are implanted into the disc space, brought together, and then locked in place.
Figure 2B:
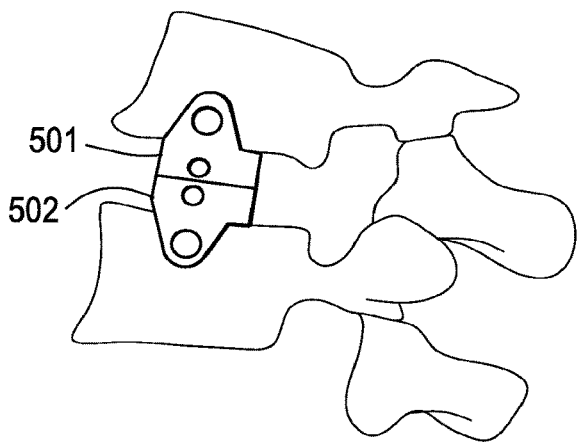
Figure 3:
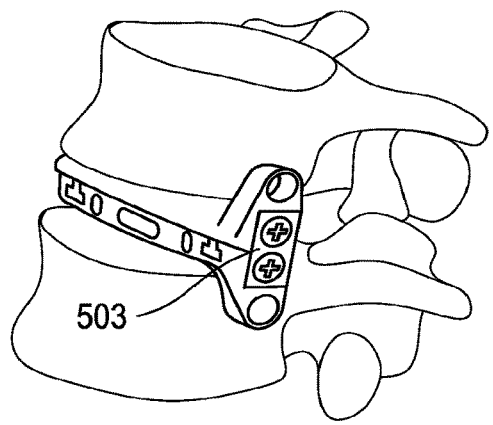
Figure 4E:
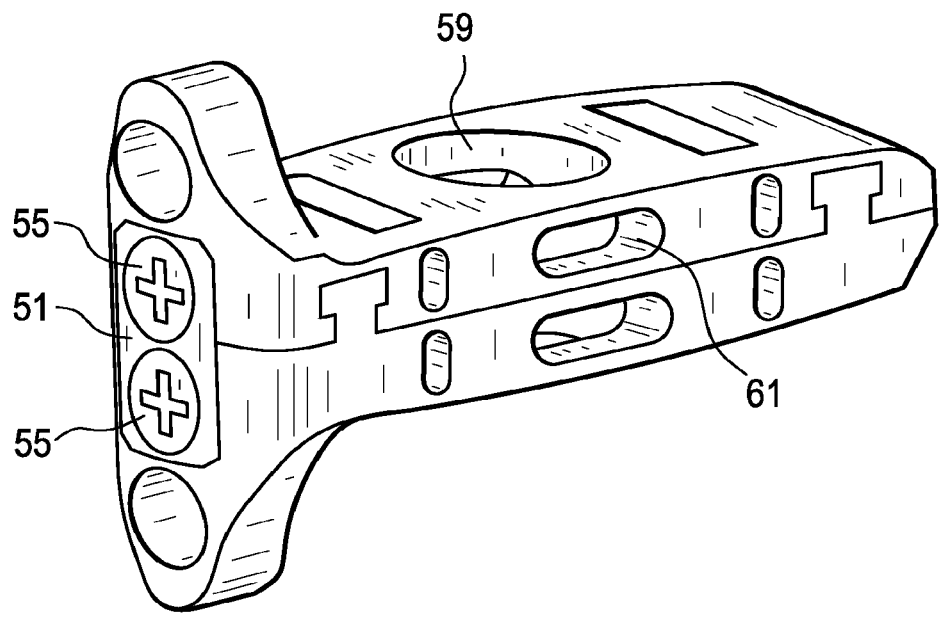
FIGS. 4e-4f show various views of the cages of an intervertebral fusion device of the present invention locked with a locking plate.
Figure 4F:
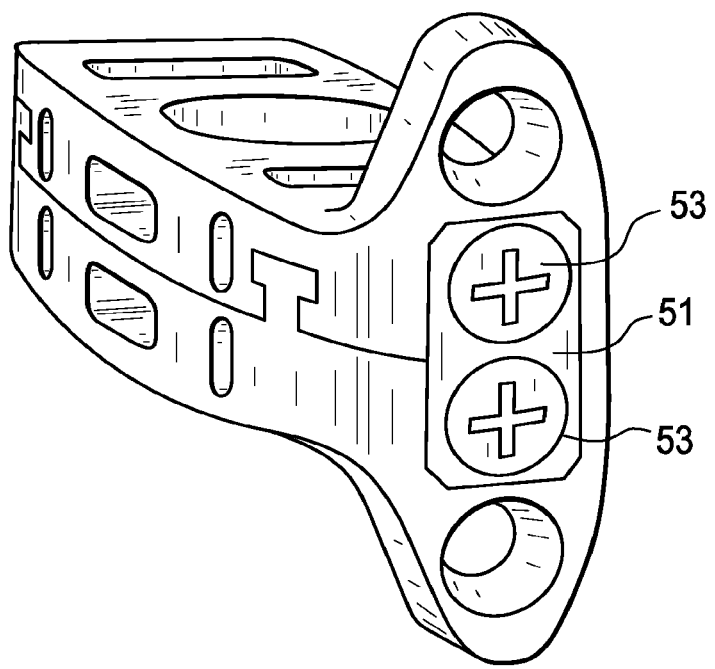

Following fixed attachment to the vertebral body, the superior and inferior cages may be aligned by several means, including the following:

FIGS. 2a-2b and 3 disclose the implantation of a first embodiment of a fusion device of the present invention, in which the cages 501, 502 of the device are implanted into the disc space, brought together, and then locked in place with a locking plate 503. FIGS. 4a-4d show various views of the intervertebral fusion device of the present invention. FIGS. 4e-4f show various views of the cages of an intervertebral fusion device of the present invention locked with a locking plate.

FIG. 2a and FIG. 2b respectively show the relative positions of the fixed cage before and after alignment. In the FIG. 2b position, the cages have properly aligned the vertebral bodies, and thereby corrected the spondylolisthesis. The superior and inferior cages can also have features that provide or enhance the connection of the cages to the compressor. These features include recesses, pilot holes and threads located on the proximal walls of the two cages (and optionally extending therethrough) that receive mating features located on the cage inserter. These features may also assist in the alignment of the cages. Lastly, the upper portion of the proximal wall of the upper cage and the lower portion of the proximal wall of the lower cage each extend past the anterior and posterior walls of the respective cages, and each has a transverse throughhole. Fixation screws may extend through these holes and into the lateral walls of the corresponding vertebral bodies to provide the immediate fixation of the cages to these vertebral bodies. Such screw locking features are well known in the art.

As shown in FIGS. 4a, 4b and 4d, the superior and inferior cages together preferably form a dovetail joint (or other joint having an expanding recess) that allows linear anterior-posterior relative movement of the fixed cages to effect the desired alignment of the vertebral bodies. The contacting surfaces of the superior and inferior cages may also have matching ratchet teeth, as in FIG. 4d, that provide incremental adjustment of the relative cage positions, and the short term inter-cage securement following the compression.

As shown in FIGS. 4e and f, once the superior and inferior cages are aligned together, this desired position may be fixed by attaching a single locking plate to the proximal ends of each cage. This locking plate may be attached to the cages by passing screws through the holes in the plate and into the corresponding holes in the lower portion of the proximal wall of the upper plate and the upper portion of the proximal wall of the lower plate.

Now referring to FIGS. 4a-4f, there is provided (claim 1) an intervertebral fusion device for correcting spondylolisthesis in a patient, comprising:

a) an upper cage 1 having an anterior wall 3, a posterior wall 5, and a proximal wall 7 and a distal wall 9 connecting the anterior and posterior walls, and an upper surface 11 for contacting an upper vertebral body and a lower surface 13, b) a lower cage 15 having an anterior wall 17, a posterior wall 19, and a proximal wall 21 and a distal wall 23 connecting the anterior and posterior walls, and a lower surface 25 for contacting a lower vertebral body and an upper surface 27, wherein the lower surface of the upper cage slidingly mates with upper surface of the lower cage.

In some embodiments, the lower surface of the upper plate and the upper surface of the lower cage include tongue-and-groove feature. Preferably, the tongue-and-groove feature runs from about the anterior wall to about the posterior wall. Preferably, the tongue-and-groove feature comprises an expanding recess 29 and more preferably comprises a dovetail 31.

In some embodiments, the lower surface of the upper cage and the upper surface of the lower cage include a ridge and recess feature 33 that runs in a proximal-distal direction.

In some embodiments, the proximal wall of the upper cage has a height Hu-p, the anterior wall of the upper cage has a height Hu-a, and wherein the height of the proximal wall of the upper cage is greater than the height of the anterior wall of the upper cage.

In some embodiments, the proximal wall of the upper cage has an upper portion 35 having a upper through-hole 37 located above the anterior wall and adapted for receiving a bone screw.

In some embodiments, the proximal wall of the lower cage has a height Hl-p, the anterior wall of the lower cage has a height Hl-a, and wherein the height of the proximal wall of the lower cage is greater than the height of the anterior wall of the lower cage.

In some embodiments, the proximal wall of the lower cage has a lower portion 39 having a lower through-hole 41 located beneath the anterior wall and adapted for receiving a bone screw.

In some locking plate embodiments, the proximal wall of the upper cage has a lower portion 43 having an lower through-hole 45 located beneath the anterior wall of the upper cage and adapted for receiving a screw. Likewise, the proximal wall of the lower cage has an upper portion 47 having an upper through-hole 49 located above the anterior wall of the lower cage and adapted for receiving a bone fastener such as a screw. The device further comprises:

c) a locking plate 51 having a first and second throughholes 53, and d) first and second bone fasteners (such as screws) 55, wherein the locking plate is fixed to the proximal wall of the upper and lower cages by passing the first bone fastener through the first throughhole of the locking plate and into the lower throughhole of the upper cage, and by passing the second bone fastener through the second throughhole of the locking plate and into the upper throughhole of the lower cage.

In some embodiments that promote fusion, the upper cage further comprises a lower surface 13 and a throughole 59 running from the upper surface to the lower surface. In some embodiments that promote fusion, the lower cage further comprises an upper surface and a throughole running from the upper surface to the lower surface. Likewise, the anterior wall further comprises a throughole 61 running therethrough. These throughholes are of a size adapted to promote fusion In some embodiments, the distal end wall of each of the upper and lower cages has a taper 63 for ease of insertion.

In the first embodiment, and now referring to FIGS. 5a-7b, the alignment means is compression-activated. This preferred embodiment uses a compression instrument to bring the anterior and posterior walls of the inferior and superior cages into alignment, and thereby correct spondylolisthesis.

Figure 5A:
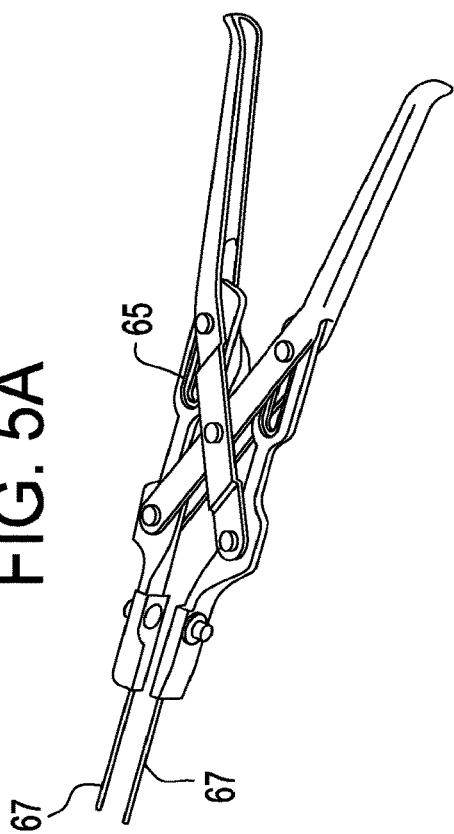
FIGS. 5a-b disclose a compression-directed inserter of the present invention having distal pins, and the insertion of a cage of the present invention with this inserter.
Figure 5B:
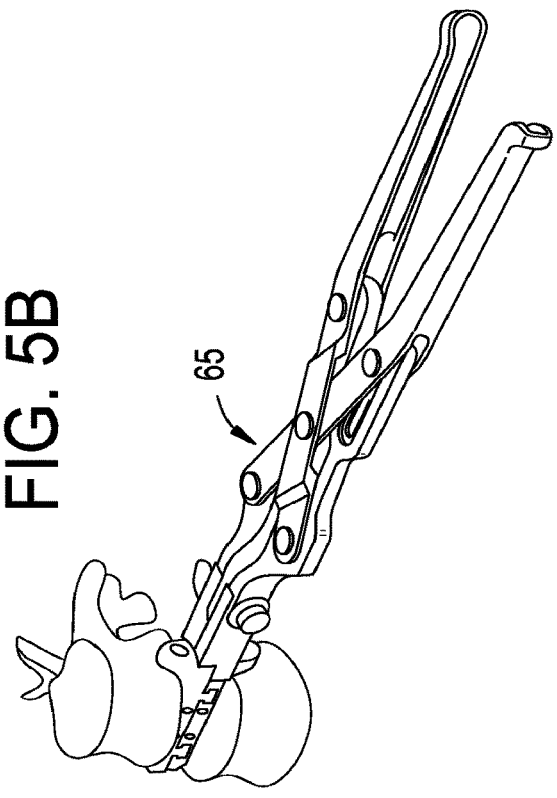
Figure 5C:
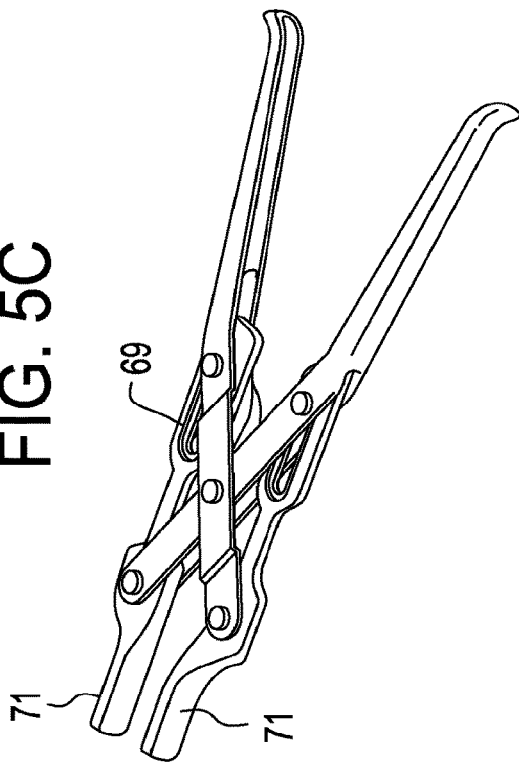
FIGS. 5c-d disclose a compression-directed inserter of the present invention having distal blades, and the insertion of a cage of the present invention with this inserter.
Figure 5D:
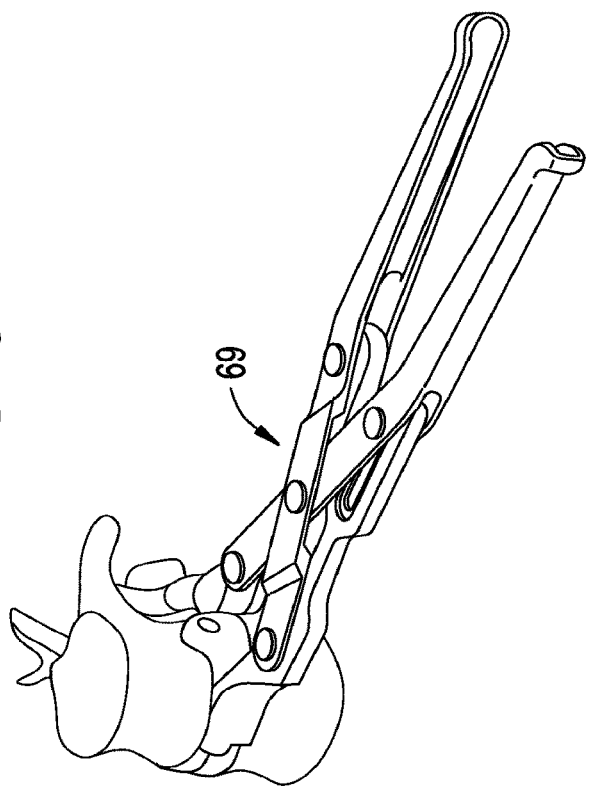
Figure 6A:
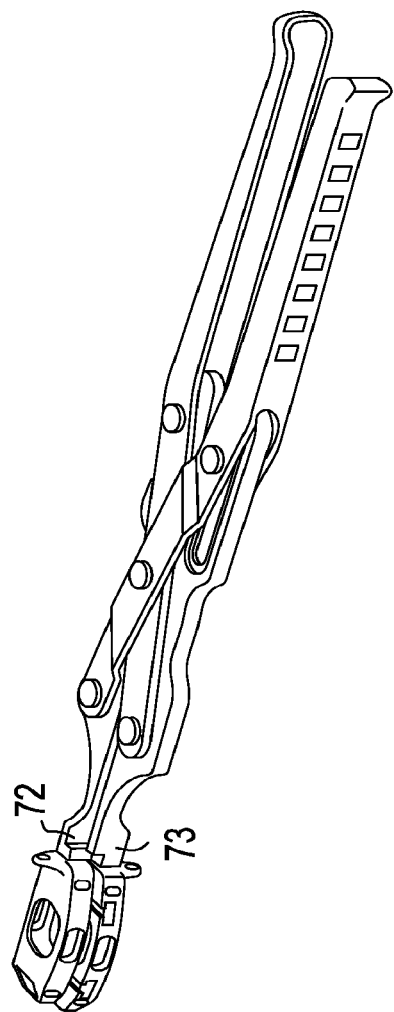
FIGS. 6a-7b disclose how a compression-directed inserter of the present invention having nested blades aligns the cages of the present invention when activated.
Figure 6B:
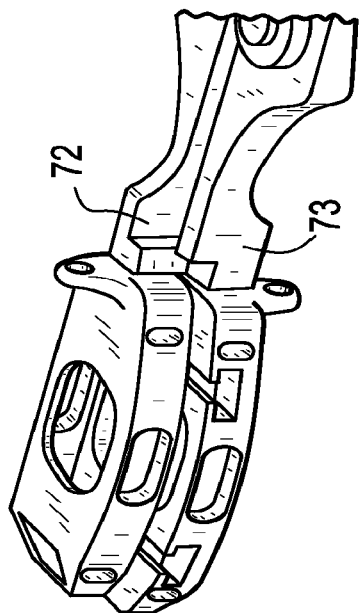
Figure 7A:
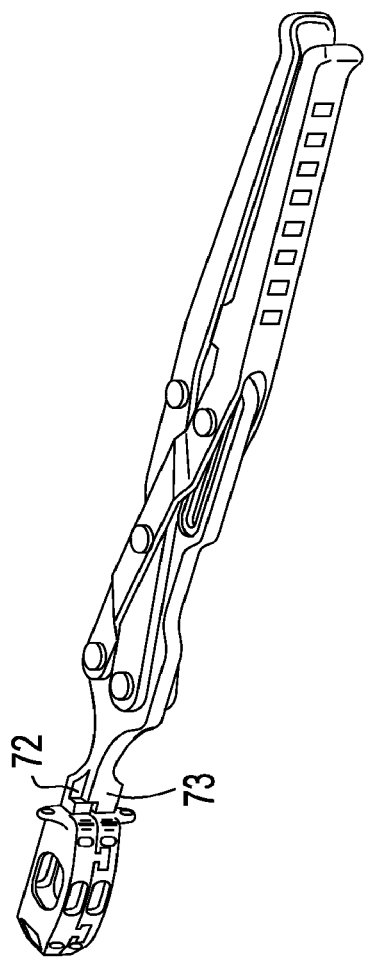
Figure 7B:
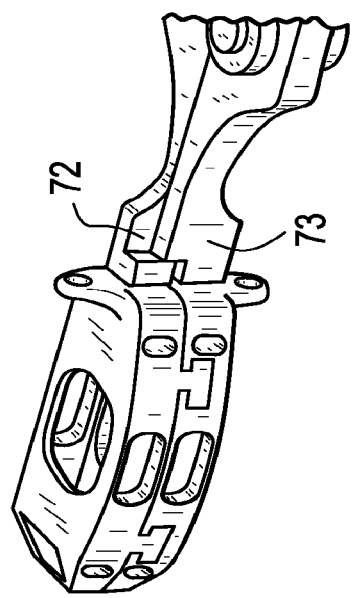

FIGS. 5a-b disclose a compression-directed inserter 65 of the present invention having distal pins 67, and the insertion of a cage of the present invention with this inserter. FIGS. 5c-d disclose a compression-directed inserter 69 of the present invention having distal blades 71, and the insertion of a cage of the present invention with this inserter. FIGS. 6a-7b disclose how a compression-directed inserter of the present invention having nested blades 72, 73 aligns the cages of the present invention when activated.

Now referring to FIG. 5a-d, the compressor instrument may have distal extensions such as blades 71 (FIG. 5c) or pins 67 (FIG. 5*a*) that act to align the anterior and posterior walls of the cages via compression. The blades of FIG. 5*c* simply push the anterior and posterior walls of the cages towards each other, thereby removing any overlap and bringing the anterior and posterior walls of these cages into vertical alignment. FIGS. 6*a*-7*b* disclose the nesting details of the distal portions of the pinned compressor instrument that allow the instrument's distal pins (not shown) to become aligned.

Therefore, in accordance with the present invention, there is provided (claim 16) a method for correcting spondylolisthesis in a patient, comprising the steps of:

a) selecting a fusion device comprising an upper cage and a lower cage, b) fixing the upper cage to an upper vertebral body of the patient and the lower cage to a lower vertebral body of the patient, c) moving the upper cage relative to the lower cage to correct the spondylolisthesis. Preferably, the method further comprises the step of: d) locking the upper cage to the lower cage. In some embodiments, the locking step is accomplished by a locking plate. In some embodiments, the moving step is accomplished with a compression-directed inserter.

In some embodiments, the moving step is accomplished with a rotary spreader.

In a second embodiment, and now referring to FIG. 8*a*-8*d*, the alignment means is rotary spreader-activated. FIGS. 8*a*-8*d* disclose how the cages of one embodiment of the present invention are aligned by a rotary spreader, and are locked by a particular locking plate. A modified spreader or shaver can be inserted into a space formed in the proximal end wall of the unaligned device. Rotating the spreader causes relative anterior-posterior movement of the upper cage vis-a-vis the lower cage to enable alignment of the cages and thereby intraoperative adjustment of a spondylosed functional spinal unit (FSU).

Figure 8A:
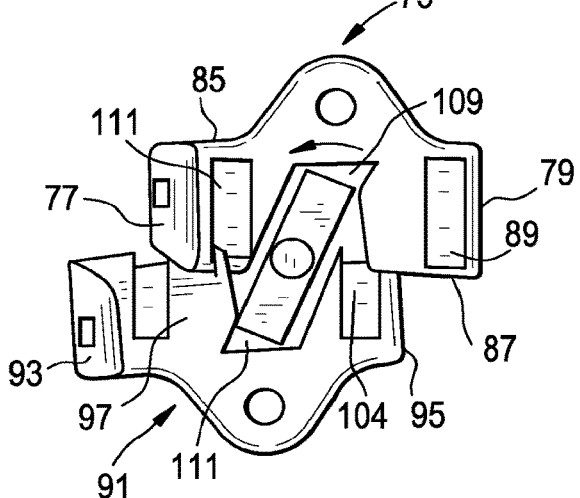
FIGS. 8a-8d disclose how the cages of one embodiment of the present invention are aligned by a rotary spreader, and are locked by a particular locking plate.
Figure 8B:
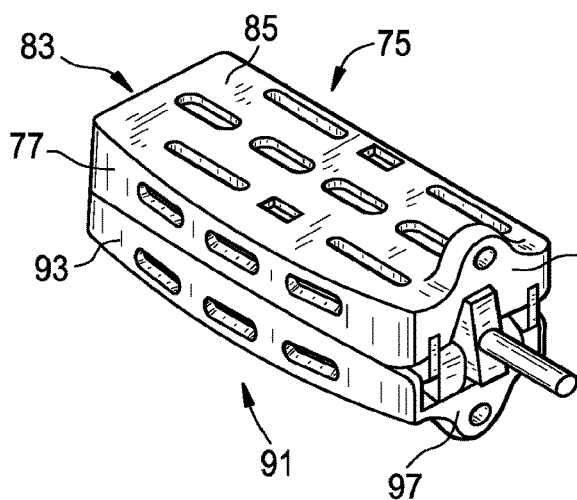
Figure 8C:
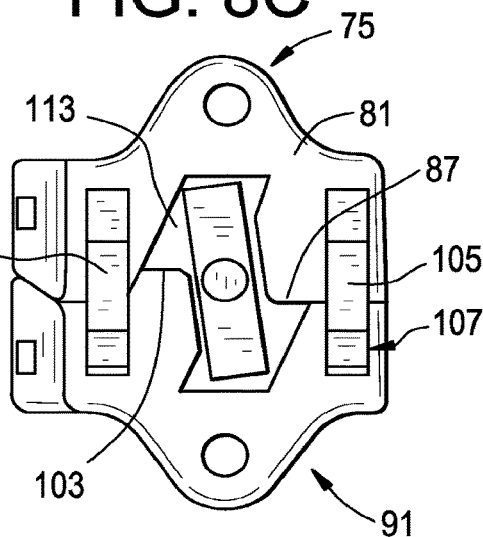
Figure 8D:
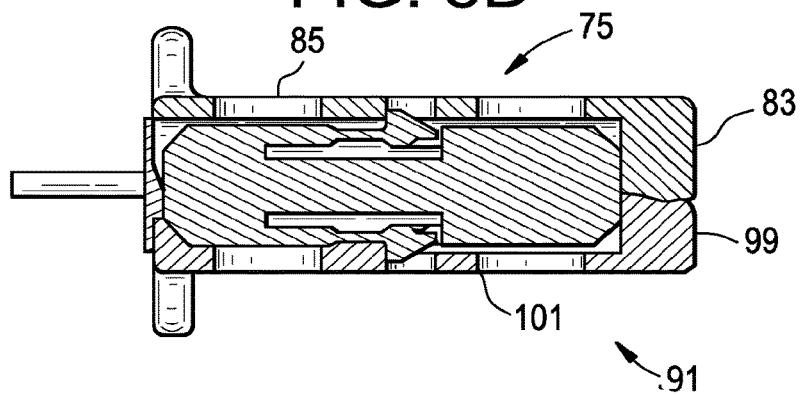

Now referring to FIG. 8*b*, optional locking plates can be employed to fix the device after the spondylolisthesis has been corrected. These plates are preferably inserted into bilateral, aligned, longitudinal recesses that extend across the interface of the aligned cages to provide inter-cage locking. In some embodiments, these plates are locked into place via a snap-lock mechanism, as shown in FIG. 8*d*.

In some embodiments, and now referring to FIG. 8*a*, the upper surface of the lower cage and the lower surface of the upper cage may be configured in matching domes in order to mimic the natural relative arced movement of adjacent vertebral bodies.

Now referring to FIGS. 8*a*-8*d*, there is provided (claim 21) an intervertebral fusion device for correcting spondylolisthesis in a patient, comprising:

a) an upper cage 75 having an anterior wall 77, a posterior wall 79, and a proximal wall 81 and a distal wall 83 connecting the anterior and posterior walls, and an upper surface 85 for contacting an upper vertebral body and a lower surface 87 having a first groove 89 therein, b) a lower cage 91 having an anterior wall 93, a posterior wall 95, and a proximal wall 97 and a distal wall 99 connecting the anterior and posterior walls, and a lower surface 101 for contacting a lower vertebral body and an upper surface 103 having a second groove 104 therein, and c) a pair of locking plates 105, wherein the lower surface of the upper cage contacts the upper surface of the lower cage so that the first and second grooves form a first throughhole 107 running from the proximal wall to about the distal wall, wherein the locking plate is disposed in the first throughole.

In some embodiments, the first groove is present upon the lower surface of the anterior wall of the upper cage, and the second groove is present upon the upper surface of the anterior wall of the lower cage. In other embodiments, the first groove is present upon the lower surface of the posterior wall of the upper cage, and the second groove is present upon the upper surface of the posterior wall of the lower cage.

In some embodiments, the device of the second embodiment further comprises a third groove 109 present upon the lower surface of the upper cage between the anterior and posterior walls, and a fourth groove 111 present upon the upper surface of the lower cage between the anterior and posterior walls, and wherein the lower surface of the upper cage contacts the upper surface of the lower plate so that the third and fourth grooves form a second throughhole 113 running from the proximal wall to about the distal wall, the second throughhole adapted for insertion of a spreader therein.

In a third embodiment, and now referring to FIGS. 9*a*-9*g*, the attachment means is linkage activated. FIGS. 9*a*-9*g* disclose various views of a dual linkage embodiment of the present invention Single- or double-linkage can be used to correct spondylolisthesis by moving this cage from a pre-activated (FIG. 9*a*) to a post-activated state. (FIG. 9*b*) In some linkage embodiments, the anterior and posterior walls of the cages also function as linkage bars, providing for pivoting connection with both an upper wall component and a lower wall component to allow for relative anterior-posterior movement of the upper wall vis-a-vis the lower wall and thereby spondylolisthesis correction.

Figure 9A:
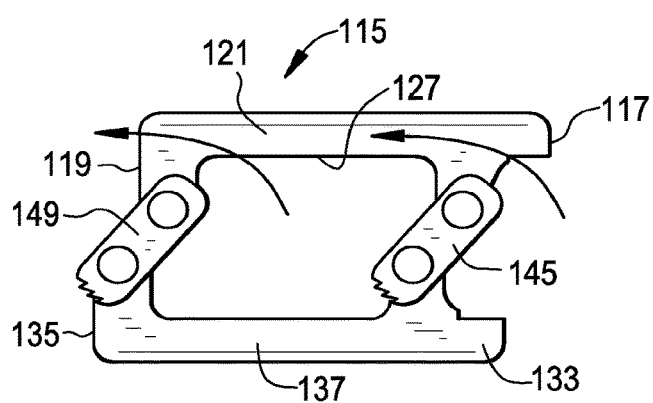
Figure 9B:
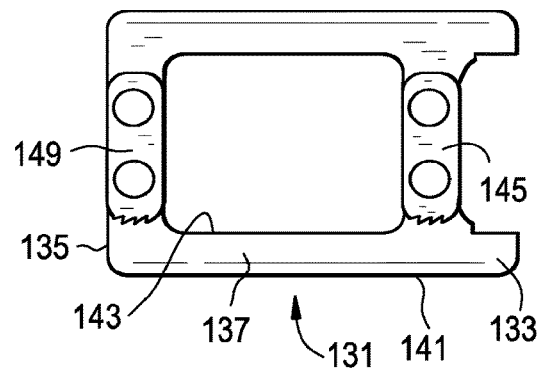
Figure 9C:
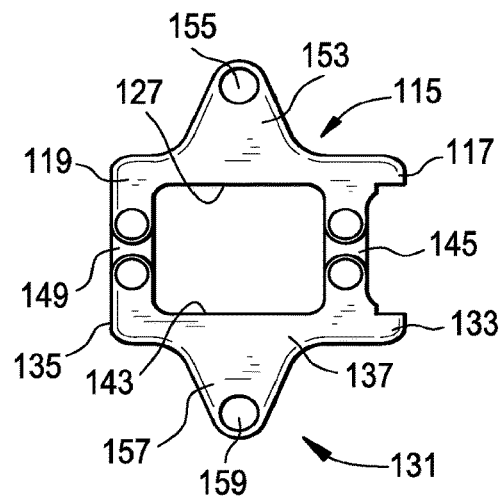
Figure 9D:
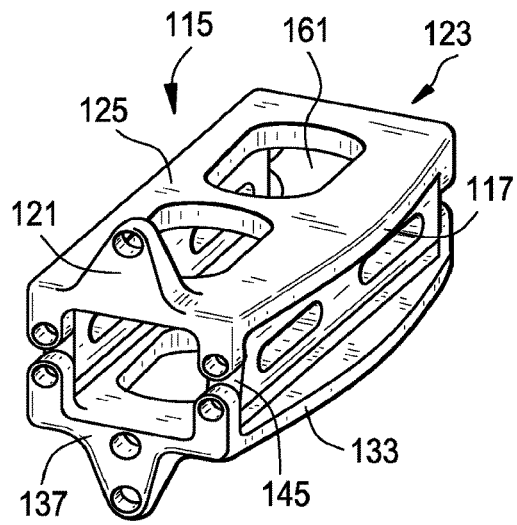
Figure 10A:
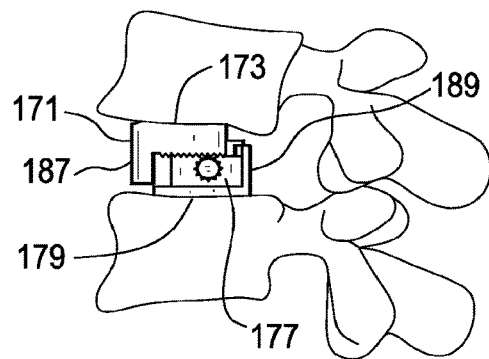
FIGS. 10a-d disclose full and partial views of a rack-and-pinion embodiment of the present invention, some of which are inserted into a disc space.
Figure 10B:
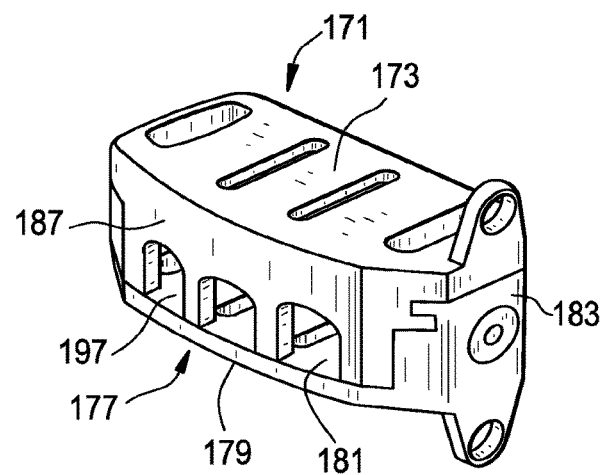
Figure 10C:
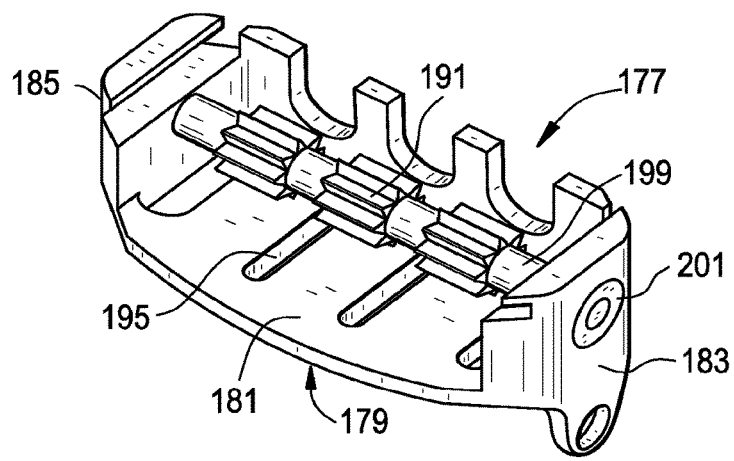
Figure 10D:
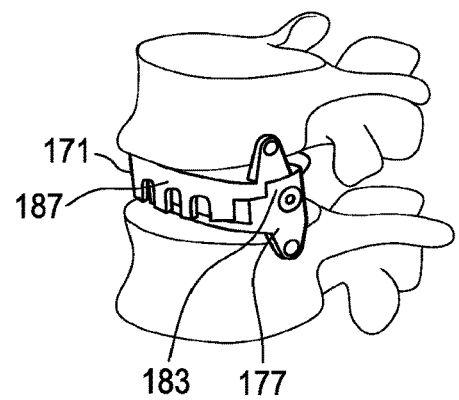

In some embodiments, and now referring to FIGS. 9*c*-9*d*, the upper portion of the upper wall and the lower portion of the lower wall extend outwardly, and transverse holes in these portions provide a means to fix the upper and lower walls to the respective lateral walls of the vertebral bodies.

In some embodiments, and now referring to FIG. 9*d*, the upper wall and the lower wall have transverse throughholes that extend into a chamber formed in the interior of the device. These throughholes and this chamber facilitate the fusion of the opposing vertebral bodies through the device. Also referring to FIG. 9*d*, the anterior and posterior walls may likewise have transverse throughholes that extend into a chamber formed in the interior of the device, and thereby facilitate the fusion of the opposing vertebral bodies through the device.

Now referring to FIG. 9*e*-9*g*, optional locking plates can be employed to fix the device following spondylolisthesis correction. These plates are preferably inserted into bilateral, aligned, longitudinal recesses that extend from the upper wall to the lower wall to provide inter-cage locking. In some embodiments, these plates are locked into place via a snap-lock mechanism, as shown in FIG. 9*e*.

Now referring to FIGS. 9*a*-9*g*, there is provided (claim 31) an intervertebral fusion device for correcting spondylolisthesis in a patient, comprising:

a) an upper cage 115 having an anterior wall 117, a posterior wall 119, and a proximal wall 121 and a distal wall 123 connecting the anterior and posterior walls, and an upper surface 125 for contacting an upper vertebral body and a lower surface 127, b) a lower cage 131 having an anterior wall 133, a posterior wall 135, and a proximal wall 137 and a distal wall 139 connecting the anterior and posterior walls, and a lower surface 141 for contacting a lower vertebral body and an upper surface 143, wherein the anterior wall is connected to the proximal wall by a first dual linkage 145 and to the distal wall by a second dual linkage (not shown), wherein the posterior wall is connected to the proximal wall by a third dual linkage 149 and to the distal wall by a fourth dual linkage (not shown), wherein the linkages allow the upper plate to pivot relative to the lower plate in the plane of the proximal wall.

In some aspects of this third embodiment, the proximal wall of the upper cage has a height, the anterior wall of the upper cage has a height, and wherein the height of the proximal wall of the upper cage is greater than the height of the anterior wall of the upper cage. In some embodiments thereof, the proximal wall of the upper cage has an upper portion 153 having a upper through-hole 155 located above the anterior wall and adapted for receiving a bone screw.

In other aspects of this third embodiment, the proximal wall of the lower cage has a height, the anterior wall of the lower cage has a height, and wherein the height of the proximal wall of the lower cage is greater than the height of the anterior wall of the lower cage. In some embodiments thereof, the proximal wall of the lower cage has a lower portion 157 having a lower through-hole 159 located beneath the anterior wall and adapted for receiving a bone screw.

In some embodiments, the upper cage has a throughole 161 running from the upper surface to the lower surface. This throughhole is adapted for promoting fusion In a fourth embodiment, the alignment means includes a rack-and-pinion. A pinion located between the upper and lower walls and extending laterally can be rotated to move racks extending in the anterior-posterior direction and thereby reduce spondylolisthesis. FIGS. 10a-d disclose full and partial views of a rack-and-pinion embodiment of the present invention, some of which are inserted into a disc space. FIGS. 11a-11e disclose various views of the rack-and-pinion embodiment of the present invention.

Now referring to FIG. 10a-11e, there is provided (claim 41) an intervertebral fusion device for correcting spondylolisthesis in a patient, comprising:

a) an upper wall 171 having an upper surface 173 adapted for contacting an upper vertebral body and an inner surface 175, b) a lower wall 177 having a lower surface 179 adapted for contacting a lower vertebral body and an inner surface 181, c) proximal 183 and distal 185 walls extending between the upper and lower walls, d) anterior 187 and posterior 189 walls extending between the upper and lower walls, e) a rack-and-pinion mechanism located between the inner surfaces of the upper and lower walls wherein the pinion 191 extends substantially from the distal wall to the proximal wall, wherein the rack 193 extends substantially from the anterior wall to the posterior wall, so that rotation of the pinion effects relative movement of the upper and lower walls in the anterior-posterior direction.

In some aspects of the fourth embodiment, the length of the device is at least three times the height of the device.

In some embodiments, the upper and lower walls each have at least one hole 195 therethrough to facilitate fusion through the device. In others, the anterior and posterior walls each have at least one hole 197 therethrough to facilitate fusion through the device.

In some embodiments, the rack extends from the inner surface of the upper wall. In others, the rack extends from the inner surface of the lower wall.

In some embodiments, the pinion comprises a proximal end 199 having a feature 201 for receiving a rotary tool.

In some embodiments, at least one of the anterior and posterior walls is integral with at least one of the upper and lower walls.

In some embodiments, at least one of the anterior and posterior walls is removable.

The embodiments of the present invention may optionally a securement plate that attaches to both the device of the present invention and the vertebral bodies. This securement plate secures the position of the device and provides supplemental stabilization.

In general, the devices of the present invention are suited for substantially lateral insertion into the disc space. In some embodiments, the cages are inserted through a more anterolateral insertion angle.

Now referring to FIGS. 4a and 4c, the length L of the device is characterized as the distance from the distal wall to the proximal wall. The width W of the device is characterized as the distance from the anterior wall to the posterior wall. The height H of the device is characterized as the distance from the lower surface to the upper surface, excludes the upper and lower portions that extend past the anterior wall, and generally corresponds to the height of the disc space. In general, the length of the lateral devices of the present invention are typically at least twice and often three times the width of the device. In general, the length of the lateral devices of the present invention are typically at least twice and often three times the height of the device. Typically, the width of the device is greater than the height of the device.

Figure 11A:
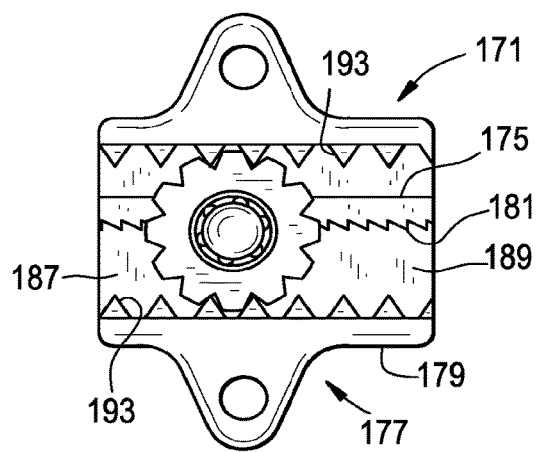
FIGS. 11a-11e disclose various views of the rack-and-pinion embodiment of the present invention.
Figure 11B:
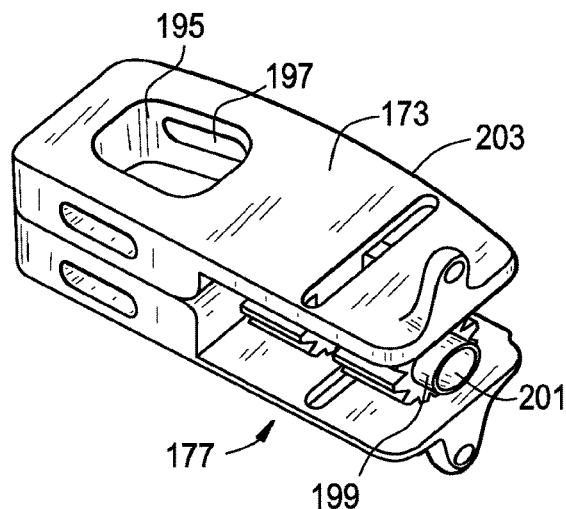
Figure 11C:
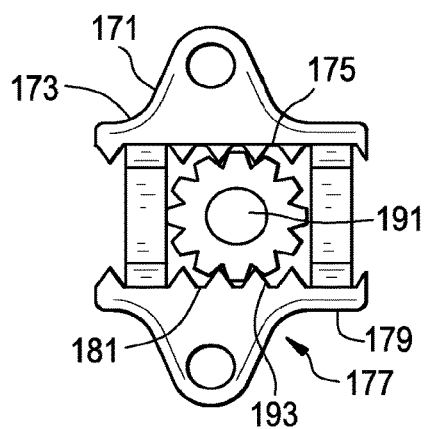
Figure 11D:
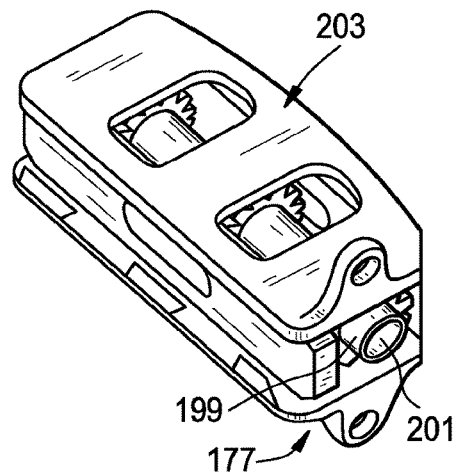
Figure 11E:
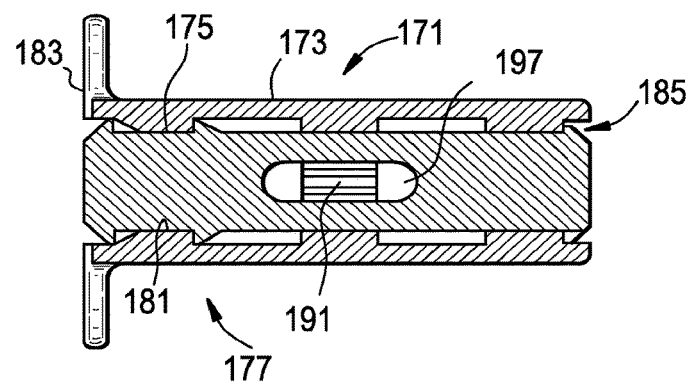

In some embodiments, as in FIG. 11b, the anterior wall of the cage may have a convex curve 203 to mimic the convex shape of the anterior portion of the disc space The lateral spondylolisthesis reduction fusion devices of the present invention may be produced from a single material or from multiple materials. These materials include metallics (such as Ti, Ti alloys such as nitinol, stainless steel, and cobalt-chrome), polymeric materials (including PEEK, PEAK, polypropylene, polyethylene terephthalate (PET), UHMWPE), biologic materials (including allograft, hydroxyapatite, TCP and CaPO$_4$), and ceramic materials including silicon nitrides, and zirconia-containing ceramics. The plate, fasteners, or locking mechanisms can be produced from metallics or polymers for enhance durability.

Additionally, modified versions of this concept can be designed to correct spondylolisthesis with superior and inferior cages that are inserted from the anterior, anterior-lateral or posterior approaches.

The cages of the present invention are preferably inserted either from a right lateral or left lateral approach.

Following standard access and disc preparation procedures, the superior and inferior cages are inserted and affixed to the opposed vertebral bodies with screws or bone fasteners. Spondylolisthesis correction is then performed with the disclosed compressor or with a rotary tool. Optionally, locking members are then applied to the superior and inferior cages to fix the orientation of the segments.

Also in accordance with the present invention, there is provided a method of implanting an intervertebral device between opposed vertebral bodies, comprising the steps of:

i) selecting an intervertebral device comprising:
  a. an upper half component having an anterior wall, a posterior wall, and two side walls connecting the anterior wall and posterior wall;
  b. a lower half component having an anterior wall, a posterior wall, and two side walls connecting the anterior wall and posterior wall;
ii) inserting the device between opposed vertebral bodies, whereby the anterior walls are not aligned,
iii) moving (preferably by pivoting) one of the components with respect to the other component so that the anterior walls are substantially aligned, and
iv) fixing the device to the opposed vertebral bodies.

In some embodiments of the present invention, the fusion device is angled to provide either lordosis or kyphosis. In embodiments in which lordosis is desired, the height of the anterior wall exceeds the height of the posterior wall. An example of such a lordotic implant is shown in FIG. 4c. In embodiments in which kyphosis is desired, the height of the anterior wall is less than the height of the posterior wall.

It is believed by the present inventors that the devices disclosed herein appear to be the first intervertebral devices having a flange that connects to a side of a vertebral body. Therefore, in accordance with the present invention, there is provided a method of inserting a fusion device between opposed vertebral bodies, comprising the steps of:
  a) selecting an intervertebral device having an anterior wall, a posterior wall and a pair of side walls connecting the anterior and posterior walls, wherein at least one of the side walls has a flange axially extending beyond the anterior wall and the posterior wall, wherein the flange has a throughhole,
  b) inserting the device between the opposed vertebral bodies, and
  c) inserting a fixation device through the throughhole to fix the device to a side of one of the opposed vertebral bodies.

Although the cages of the present invention are disclosed as having flanges that extend beyond the disc space for attachment to the sides of the opposed vertebral bodies, it is also contemplated that the cages of the present invention may be attached to the opposed vertebral bodies via zero profile throughholes. These zero profile throughholes are provided both a) at the upper edge of the proximal side wall of the upper half component and b) at the lower edge of the proximal side wall of the lower half component.

Therefore, in accordance with the present invention, there is provided an intervertebral fusion device for correcting spondylolisthesis in a patient, comprising:
  a) an upper cage having an anterior wall, a posterior wall, and a proximal wall and a distal wall connecting the anterior and posterior walls, and a throughole present at the upper edge of the proximal wall for receiving a bone fixation device,
  b) a lower cage having an anterior wall, a posterior wall, and a proximal wall and a distal wall connecting the anterior and posterior walls, and a lower surface for contacting a lower vertebral body and an upper surface, and a throughole present at the lower edge of the proximal wall for receiving a bone fixation device, wherein the lower surface of the upper cage slidingly mates with upper surface of the lower cage.

Although the above description discloses how to make and use implantable devices to correct spondylolisthesis, it is within the scope of the invention to use these devices as instruments to correct retrolisthesis as well. Therefore, in accordance with the present invention, there is provided a method for correcting spondylolisthesis in a patient, comprising the steps of:
  a) selecting an instrument comprising an upper cage and a lower cage, wherein each cage is attached to a handle
  b) attaching the upper cage to an upper vertebral body of the patient and the lower cage to a lower vertebral body of the patient (preferably with caspar pins),
  c) moving the upper cage relative to the lower cage to correct the spondylolisthesis (preferably with a distractor that engages the caspar pins), and
  d) removing the instrument from the patient.

Although the above description discloses how to make and use devices in the context of correcting spondylolisthesis, it is within the scope of the invention to use similar devices to correct retrolisthesis as well.

Figure 12:
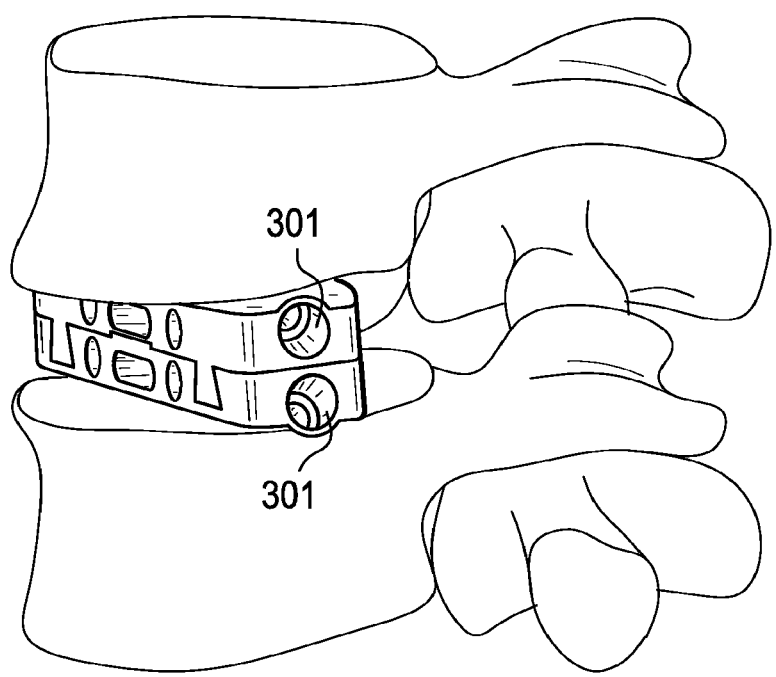
FIG. 12 discloses a lateral cage of the present invention with oblique screwholes.

FIG. 12 discloses a lateral cage of the present invention with oblique screwholes 301.

Figure 13:
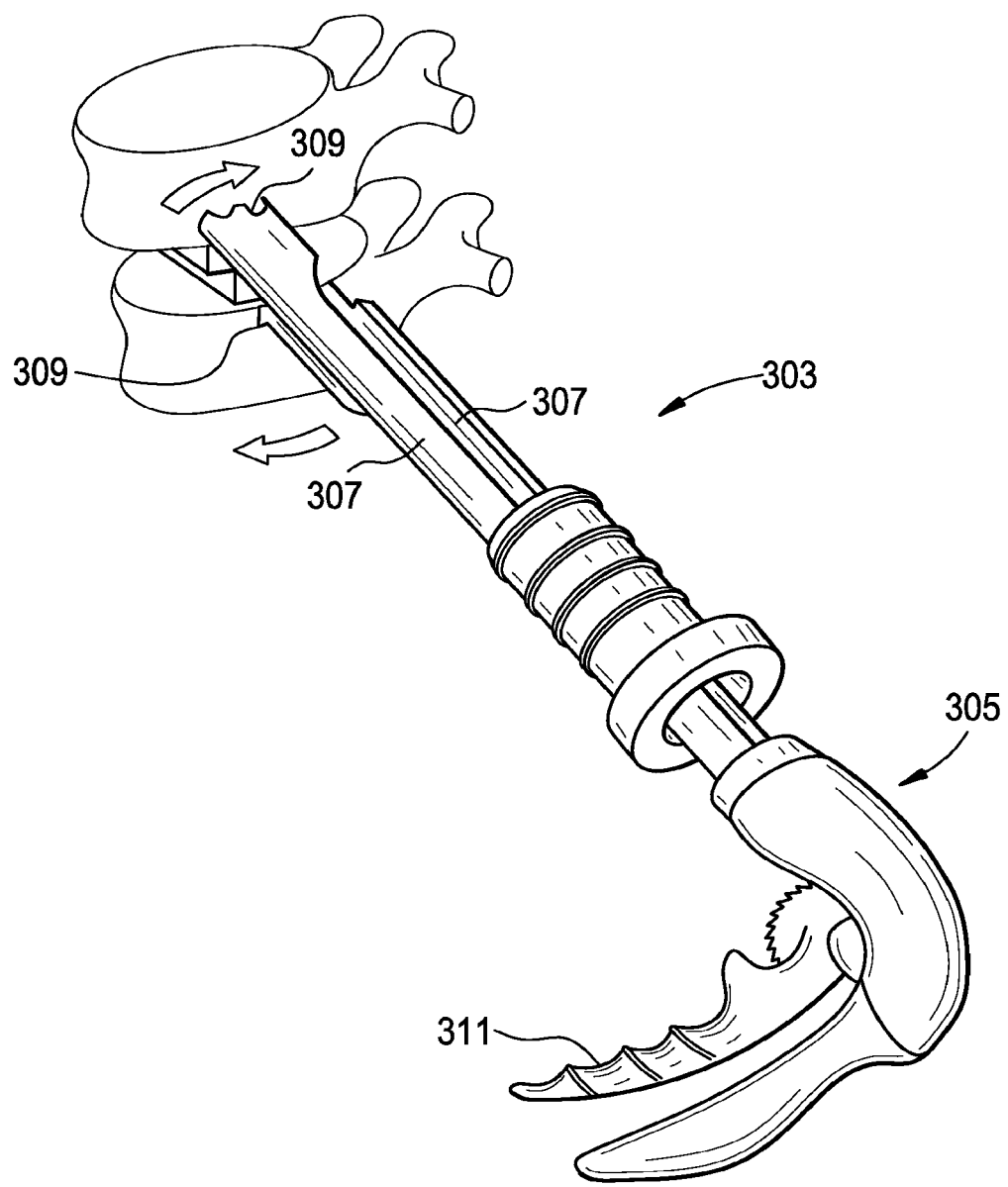
FIG. 13 discloses an inserter of the present invention.
Figure 14:
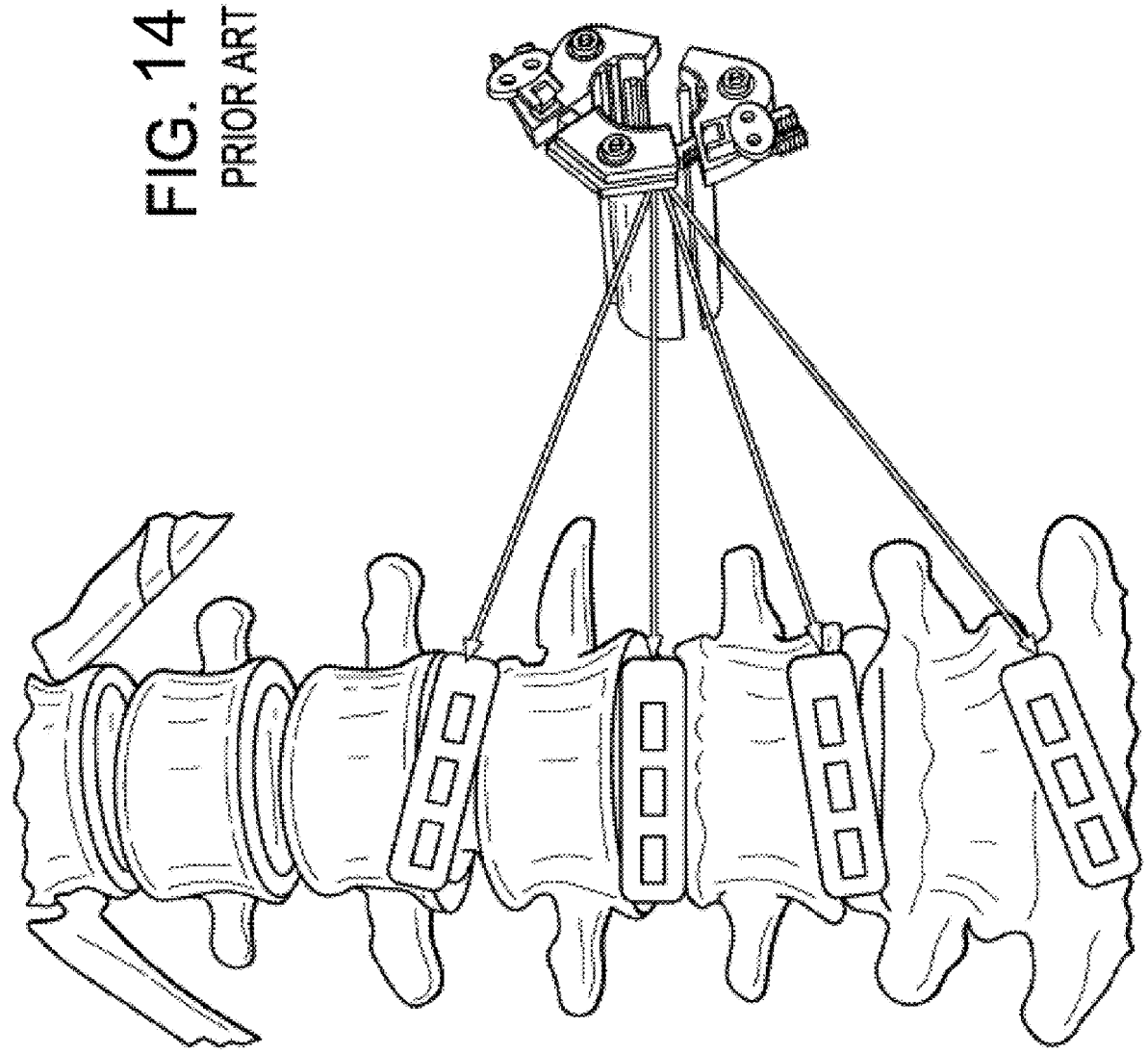
FIG. 14 discloses a coronal view of a human spine in which a conventional method of laterally implanting cages in the lower spine is used, producing malpositioned cages.

FIG. 13 discloses an inserter 303 of the present invention. FIG. 13 is a top view of a second type of spondylolisthesis reduction tool that comprises a proximal handle portion 305 and two vertebral body engaging beams 307. On the distal end of the beams are bone engaging features 309 for the respective superior and inferior vertebral bodies. At the proximal end of the beams the inferior beam is fixed within the handle and the superior is attached with a pivot so that its distal end can move posterior and anterior with respect to the lower. Conversely, the lower beam could also be affixed in a pivoting fashion so that both beams move as in a scissor fashion. This intended motion corresponds to a posterior transverse plane motion of the superior vertebral body in order to reduce the spondylolisthesis. By slightly rotating the handle or tilting the tool prior to engagement, a saggital plane component is introduced to the reduction motion (it may be beneficial to increase the height of one body over the other as you move that body posteriorly).

The cross section of the beams are sufficiently wide in the anterior-posterior direction making them resistant to bending in the transverse plane. The mechanism within the handle is to pivot the beams. This can be done with a ratchet and pawl linkage which moves the top beam one click with each squeeze, or a sliding collar that advances distally along the beams to bring them in line with each other, or a wedge/roller that advances along the edge of the superior beam or a post and angled slot mechanism that aligns the two beams, or with a geared scissor mechanism such that the full motion of the handle corresponds to a small angular change of the beams. The controlled motion of the beams relative to each other is advantageous as the operating surgeon generally has a pre-determined amount of reduction in mind for the surgery. This amount can be determined via radiograph or inter-operatively. For example if a total of 6 mm of reduction is desired, the handle can be ratcheted 1 mm at a time until the value of 6 mm is reached. Therefore, there is provided a spondylolisthesis reduction tool comprising:
  a) a proximal handle portion, and
  b) first and second vertebral body-engaging beams having a longitudinal axis, a proximal end portion and a distal end portion, the distal end portion of each beam forming bone engaging features, wherein the proximal end portion of the first beams is fixedly attached to the handle portion, and wherein the proximal end portion of the second beam is pivotally attached to the handle portion so that the second beam can move transversely with respect to the longitudinal axis of the first beam. Preferably, the handle portion comprises a trigger 311 adapted to pivotally move the second beam.

The present invention relates to flexible spreaders and shaver devices and methods for parallel preparation of an intervertebral disc space in the context of a non-parallel access trajectory. The flexible shavers utilize curved guide tubes to enable their placement, insertion, flexing, bending and/or pivoting in the disc space.

In some embodiments, the flexible shaft can have a flexibility-imparting geometry that includes use of at least one of a) a spring (available from SS White of Piscataway, N.J.), b) a slotted tube (available from Necomed of Hicksville, Ohio), and c) a standard universal joint. Now referring to FIGS. 15A through 15D, in some embodiments, the flexible shaver 11 of this embodiment also includes a proximal handle 15, an intermediate shaft 19 comprising a universal joint 20, and a distal shaver head 23.

Therefore, now referring to FIGS. 15A through 15D, there is provided a flexible shaver 11 for preparing a vertebral endplate, comprising:
 a) a shaft 19 having a proximal end portion 21 and a distal end portion 22,
 b) a handle 15 attached to the proximal end portion of the shaft, and
 c) a shaving head 23 attached to the distal end portion of the shaft, the head comprising:
  i) an body portion 24;
  ii) a first face 25 forming a first cutting edge, and wherein the shaft comprises a universal joint 20.

Figure 15A:
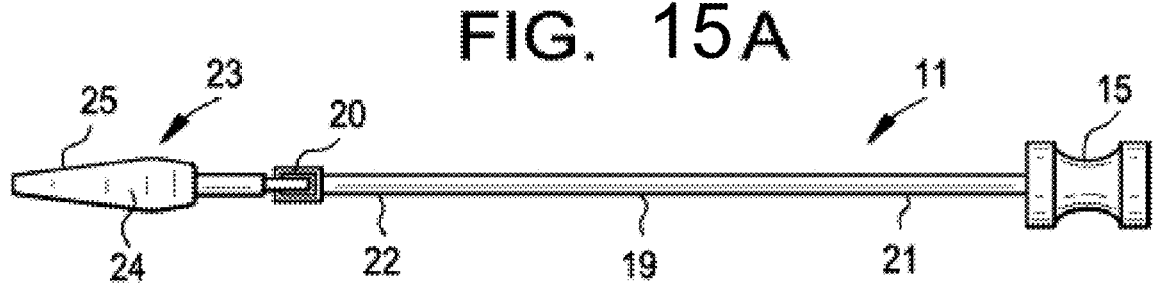
FIGS. 15A through 15C disclose various shavers of the present invention having a universal joint, wherein the shavers are presented in varying degrees of angulation.
Figure 15B:
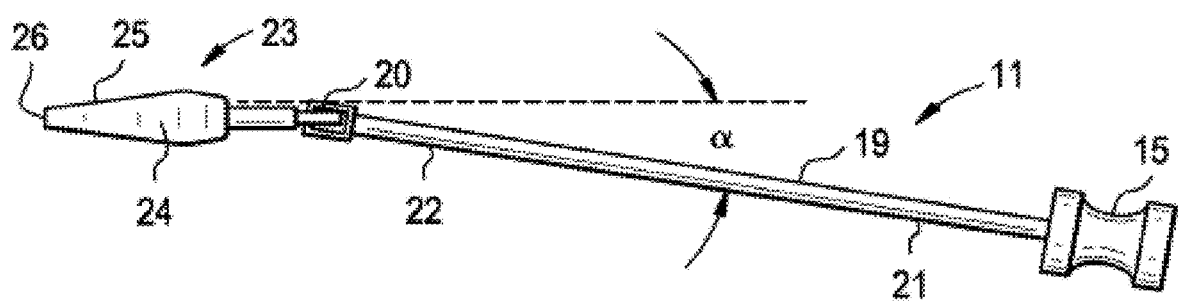
Figure 15C:
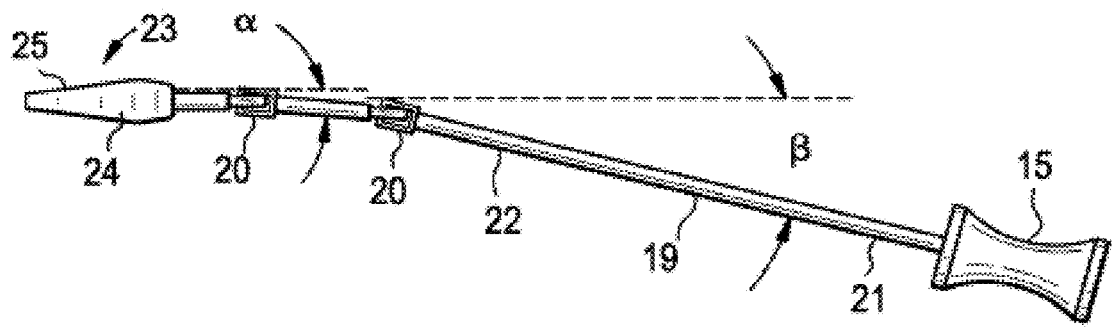
Figure 15D:
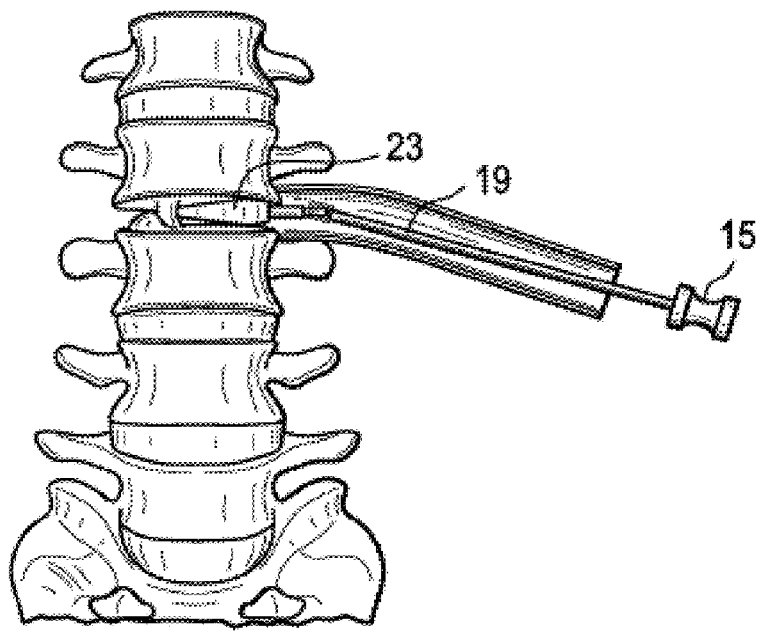
FIGS. 15D and 15E disclose a universal jointed shaver of the present invention preparing an endplate in the lower spine through a port of the present invention.
Figure 15E:
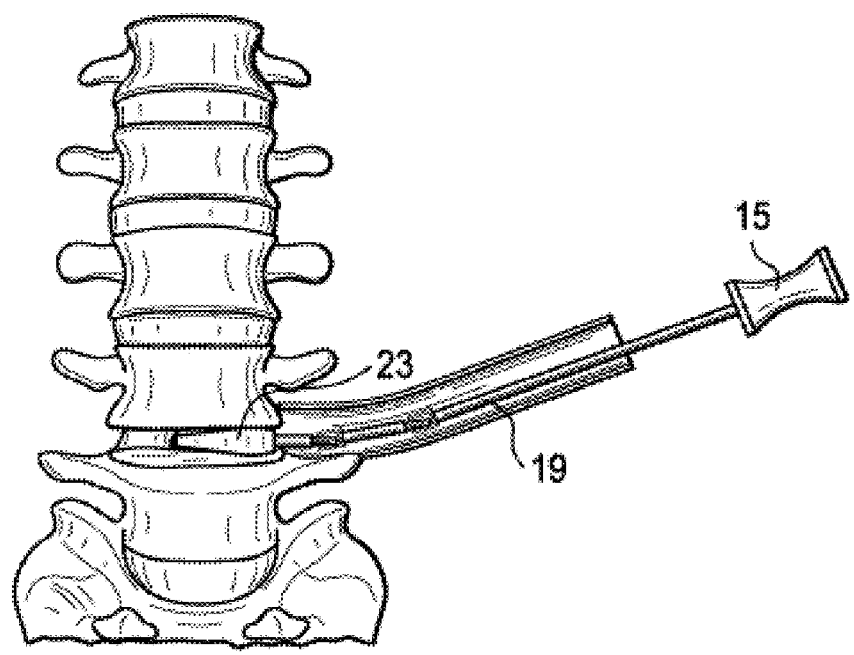

FIG. 15D shows flexible shavers 11 of this embodiment disposed within respective disc spaces, wherein the shaving heads are disposed parallel to the disc space. Therefore, use of the shaver results in shaved endplates that are substantially parallel to the natural endplates, and so will easily accommodate a lateral fusion cage without causing asymmetry.

The flexible spreader/shaver comprises a distal rigid or non-rigid shaver head having a blade. This shaver head is attached to a partially flexible drive shaft that is in turn connected to a proximal handle. The handle is rotated to turn the drive shaft and the shaving head. The flexible shaft allows variable angulations of the handle relative to the shaver blade, thereby allowing the surgeon to use an angled approach to prepare the disc space in a manner that nonetheless keeps the shaving head substantially parallel to the disc space. Typically, the shaver angulation angle α relative to the drive shaft can be up to 90 degrees, but is preferably between 10 and 45 degrees. In some embodiments, the shaving head of the flexible shaver has a bullet tip 26 for ease of entry into the disc space.

Figure 16A:
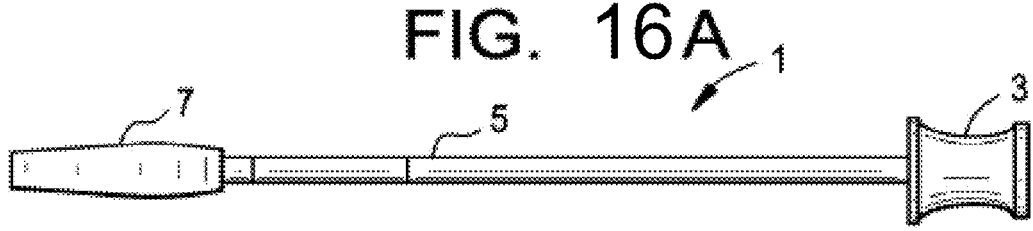
FIGS. 16A and 16B disclose various shavers of the present invention having a bendable shaft, wherein the shavers are presented in varying degrees of angulation.
Figure 16B:
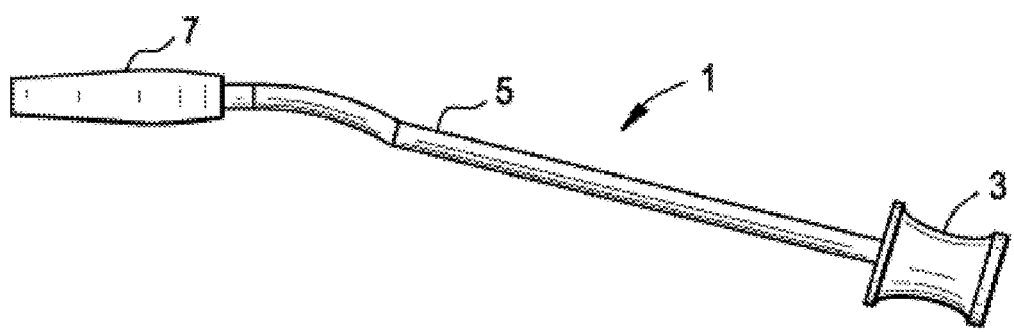
Figure 16C:
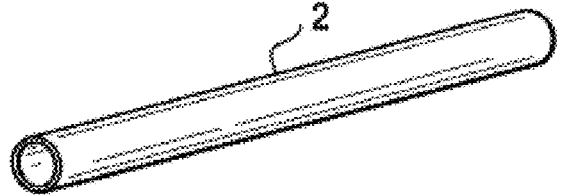
FIGS. 16C and 16D disclose a flexible port in its straight and curved configuration.

Now referring to FIGS. 16A through 16C, in some embodiments, the flexible shaver 1 of the present invention includes a proximal handle 3, an intermediate flexible shaft 5, and a distal shaver head 7. The flexible shaft can be a solid shaft made from a flexible material, or can be a spring (available from SS White of Piscataway, N.J.), or a slotted tube (available from Necomed of Hicksville, Ohio). Such flexible materials include metals such as nitinol, and polymers such as polyether ether ketone (PEEK), acrylonitrile butadiene styrene (ABS), polypropylene, and polyethylene. Stainless steels, titanium alloys, cobalt chromium alloys or combinations, mixtures and/or blends thereof. The flexible shaft may be the flexible material itself or the shaft may be constructed of strands which are wound or shafts which are slotted to impart flexibility. FIGS. 16A through 16B show a flexible shaver having a shaft made of a flexible material in its straight and curved configurations, respectively. FIG. 16C shows two flexible shavers 1 of this embodiment disposed at least partially within respective disc spaces, wherein each shaving head is disposed parallel to the disc space.

Therefore, now referring to FIGS. 16A through 16C, there is provided a method of intervertebral disc space preparation, comprising the steps of:
 a) selecting a shaver having a flexible shaft;
 b) inserting the shaver into an intervertebral disc space bounded by opposed vertebral endplates, and
 c) contacting the shaver to a vertebral endplate to cut the endplate. As shown in FIG. 16C, the use of the flexible shaver allows the shaving head to be essentially parallel to the opposed vertebral endplates. Thus, when the shaver is rotated about its longitudinal axis, the shaving head cuts in a manner parallel to the endplates, thereby preserving symmetry about the disc space.

Figure 16D:
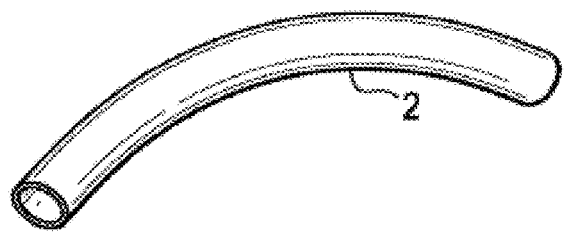
Figure 17A:
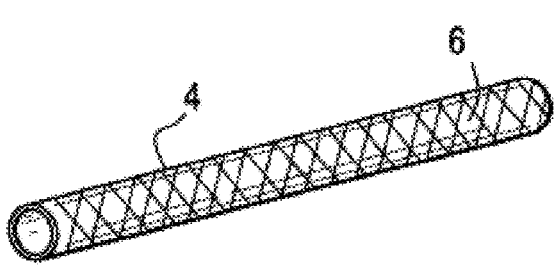
FIGS. 17A and 17B disclose a reinforced flexible port in its straight and curved configuration.
Figure 17B:
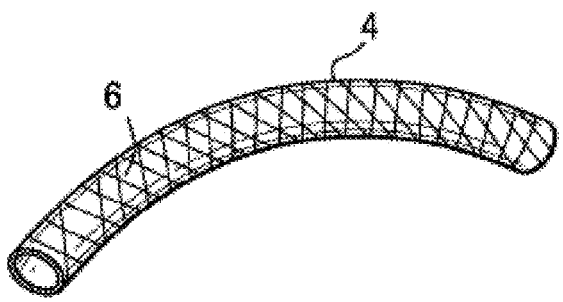
Figure 17C:
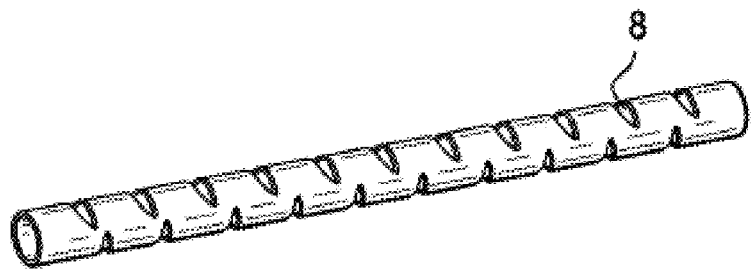
FIGS. 17C and 17D disclose a slotted port in its straight and curved configuration.
Figure 17D:
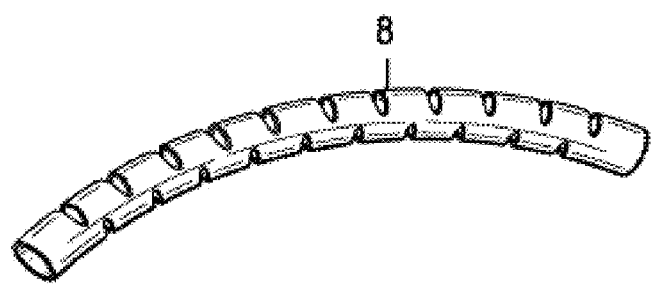

The flexible shaft can be made flexible in many different ways. For example, in some embodiments, the flexible shaft is made of a flexible material. In other embodiments, the geometry of the shaft imparts flexibility thereto. In some embodiments thereof, the flexible shaft has a universal joint. In other such embodiments, the flexible shaft is slotted to impart flexibility. In other such embodiments, the flexible shaft comprises a spring. FIGS. 16C through 16D disclose a flexible port 2 in its straight and curved configuration. FIGS. 17A through 17B disclose a flexible port 4 having reinforcements 6, the port being in its straight and curved configuration. FIGS. 17C through 17D disclose a port having slots 8 in its straight and curved configuration.

In some embodiments, a flexible port is used to dock onto a bone adjacent the disc space and thereby guide disc space preparation instruments into the disc space in a minimally invasive manner. The flexibility allows the port to curve at its distal end portion to produce a curve having an angle of, for example, 20 degrees. This curve allows a shaver to enter the port at a downward trajectory (which occurs when using a single spinal access site for multiple levels) and then orient parallel to the endplates (in order to best prepare the endplates). In some embodiments, the angle of the shaver is between 10 and 45 degrees.

Figure 18A:
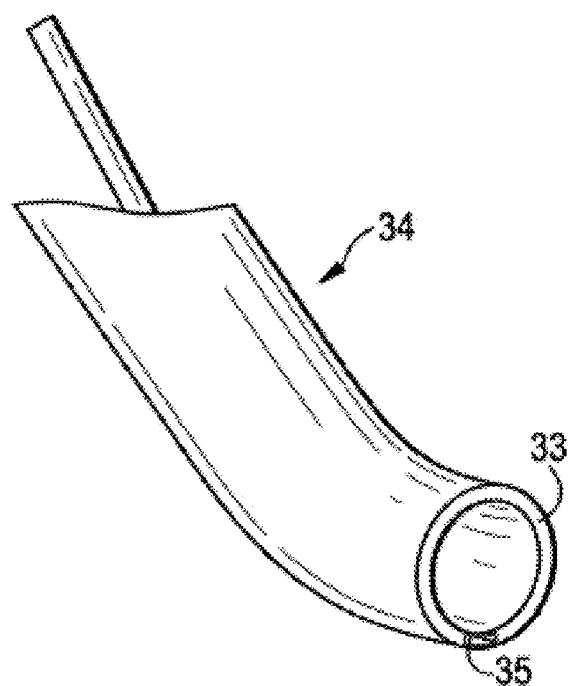
FIGS. 18A and 18B present a perspective view of a port of the present invention, wherein the securement feature is respectively retracted and advanced.
Figure 18B:
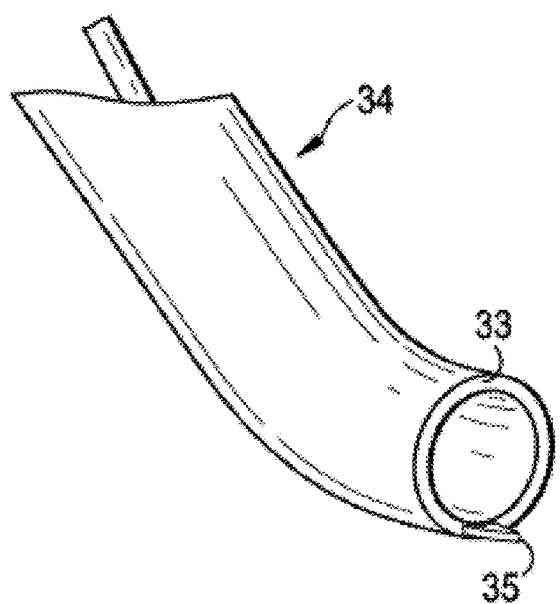

Now referring to FIGS. 18A through 18B, in some embodiments, the port may include one or more fixed or actuatable securement features 35, including a spike or teeth, extending from its distal end portion 33. These securement features fix to the bone and thereby insure secure docking of the port adjacent the target disc space. FIGS. 18A and 18B present a perspective view of a port of the present invention, wherein the securement feature 35 is respectively retracted and advanced.

Now referring to FIG. 19A through 19C, in some embodiments, the port 31 may comprise an outer cannula 34 and inserts 37 and 39. These inserts may, when installed, form an inner cannula that helps fix the orientation of the shaver when the shaver passes therethrough. Therefore, in some embodiments thereof, there is provided a port for use in preparing an intervertebral disc space, which comprises:
 a) an outer cannula 34 having a bore, and
 b) an inner cannula having a bore having a non-circular transverse cross-section, wherein the inner cannula is disposed within the bore of the outer cannula.

Preferably, the port further has features that allow it to securely dock onto the vertebral bone adjacent the disc space. Preferably, this comprises a securement feature disposed upon a distal end portion of at least one of the outer cannula and inner cannula.

In some embodiments, the port having the inner and outer cannulae has a distal end portion that is curved. In some embodiments thereof, the curve in the distal end portion is between 10 and 45 degrees. In some embodiments, the cannulae are made of flexible materials, while in others each cannula has a geometry that imparts flexibility. Because the shaver typically has a much smaller cross-section than the typical lateral cage implant, it is expected that the areal-cross section of the bore of the inner cannula will be much smaller than the areal cross-section of the bore of the outer cannula. For example, in some embodiments, the bores of the cannulae each have an areal cross section, wherein the areal cross section of the bore of the inner cannula is less than 50% of the areal cross section of the bore of the outer cannula. More preferably, the areal cross section of the bore of the inner cannula is less than 25% of the areal cross section of the bore of the outer cannula. Preferably, the inner cannula is modular in order to customize for various angles of approach and inner geometry to guide various instruments. Thus, in some such embodiments, the inner cannula comprises upper 37 and lower 39 inserts having opposing faces 38, 40. Preferably, the opposing faces each comprise a longitudinal groove 45, 46 therein. These opposing grooves may help form the bore through which the shaver passes. Therefore, these grooves dictate the orientation of the shaver passing therethrough. Preferably, the lower insert is disposed only in a curved distal end portion of the port. This allows for easier access to the disc space in the portion of the port in which shaver head orientation is not critical.

In one particular embodiment thereof, the port comprises an outer cannula having a bore, and an inner cannula (disposed within the bore of the outer cannula) having internal guiding features. In these embodiments, these internal guiding features (such as grooves 45, 46 and ridges) only allow the shaver is to be inserted into the disc space in such an orientation that the cutting surface of the shaver is parallel to the disc space.

The port can have variable distal angulations β within its distal end portion to ensure "snug" docking and control shaver angulations. The internal geometry of inserted or assembled port directs shaver into the disc space and maintains the axis of rotation.

Still referring to FIGS. 19A through 19C, in some embodiments, there is provided a port for use in preparing an intervertebral disc space, which comprises a longitudinal bore 51 therethrough, the bore having a proximal end portion 53 having a transverse cross-section and a distal end portion 55 having a transverse cross-section, wherein the transverse cross-section of the proximal end portion of the bore is greater than that transverse cross-section of the distal end portion of the bore. The requirement that the transverse cross-section of the proximal end portion of the bore is greater than that transverse cross-section of the distal end portion of the bore provides the surgeon with greater room in the proximal section of the bore to maneuver the instruments, while insuring that the instrument is still properly oriented by the time it passes through the distal end of the port.

Preferably, the port having the larger proximal bore has a distal end portion that is curved in order to insure proper orientation of the instruments passing therethrough. Preferably, the curve in the distal end portion is between 10 and 45 degrees.

In some embodiments, the transverse cross-section of the proximal end portion of the bore is defined by an upper insert, and the transverse cross-section of the distal end portion of the bore is defined by a lower insert and an upper insert. These embodiments possess larger proximal bores whose advantages are discussed above. The inserts may be tailored to specifically and particularly accommodate and orient the different instruments that enter the port.

Thus, now referring to FIGS. 19A through 19C and 20A through 20C, in some embodiments, there is provided a port for use in preparing an intervertebral disc space, comprising:
a) an outer cannula 34 having a bore 36 having a proximal end portion 65 and a distal end portion 67,
b) an upper insert 37 disposed at least in the distal end portion of the bore, and
c) a lower insert 35 disposed at least in the distal end portion of the bore.

Preferably, the lower insert is disposed only in the distal end portion of the bore. Its absence in the proximal portion provides room for the surgeon to maneuver the shaver in the proximal portion of the port. Preferably, the upper insert is disposed in both the proximal and distal end portions of the bore. This is advantageous because it improves the ease and insertion along the entire length and provides the superior internal geometry to control insertion angle and axis of rotation. Preferably, the proximal end portion of the bore is straight, and the distal end portion of the bore is curved. The straight proximal end portion of the bore allows for accurate placement of the distal end portion of the port near the target disc space. Preferably, the distal end portion of the upper insert has a face 38, and the lower insert has a face 40, and the faces oppose each other, thereby forming a bore therebetween that dictates the orientation of the shaver passing therethrough.

Figure 20C:
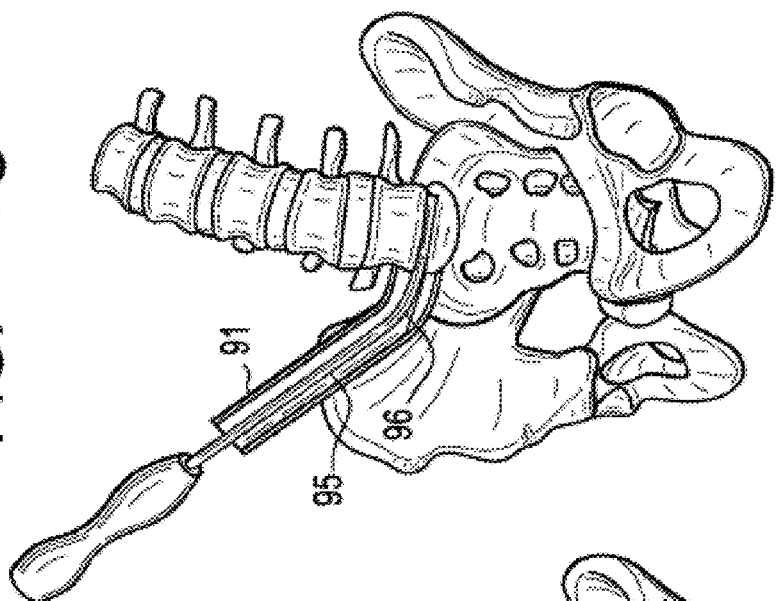
FIGS. 20A through 20C disclose advancing a shaver through the docked port of FIG. 19C.
Figure 20B:
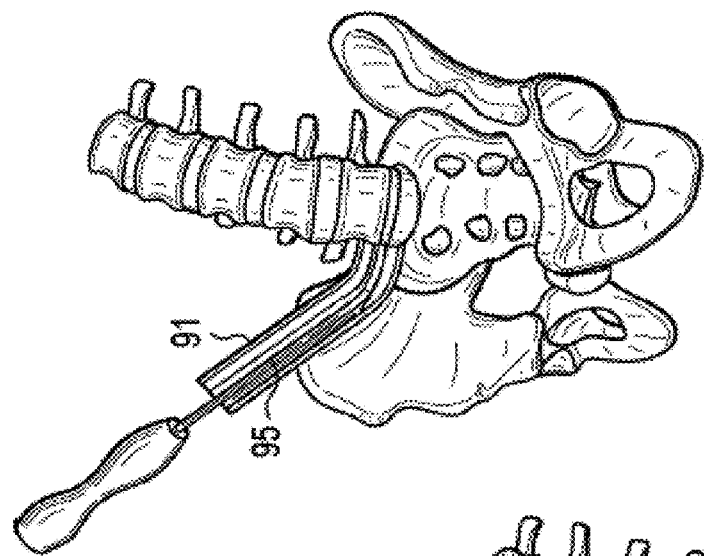
Figure 20A:
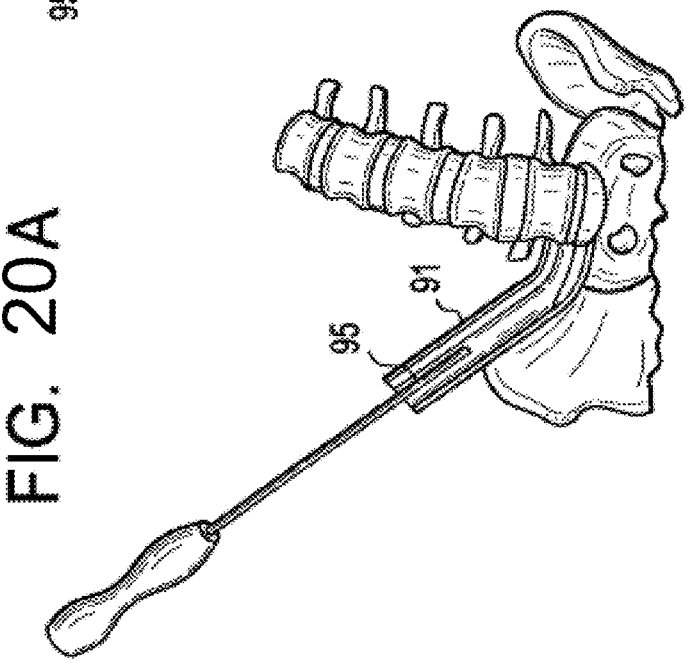

Thus, and now referring to FIGS. 20A through 20C, there is provided an assembly comprising:
a) a curved port 91 having a bore having a transverse cross-section; and
b) a vertebral endplate shaver 95 having a transverse cross-section, wherein the shaver is disposed within the bore of the curved port, wherein the transverse cross-section of the bore substantially corresponds to the transverse cross-section of the shaver so as to determine the orientation of the shaver within the bore.

In some embodiments, the curved port has a distal end portion 33 having a securement feature 35 for securing the curved port to vertebral bone adjacent the target disc space. Preferably, the shaver is bendable so that it can pass through the curved portion of the port. In some embodiments thereof, the bendable shaver has a shaft 96 made of a flexible material, while in others the bendable shaver has a shaft having a universal joint.

In one prophetic method of practicing the present invention, the curved port enters the patient through an incision made in the skin. It then proceeds towards the target disc by manual advancement. Once in the general area of the target disc, the distal portion 33 of the port is then bent by advancing it over a steerable catheter that has itself been bent (as explained below). This leaves the distal end portion of the port adjacent the target disc. The securement tooth is advanced into a neighboring vertebral body to stabilize port placement. After the disc space is cleared, the flexible shaver is then advanced through the curved port and into the disc space. The inner features of the curved port guide the shaver's angulation with respect to the disc space. Once the shaver has been suitably placed, the handle and drive shaft of the shaver are rotated to scrape disc tissue and endplates in a plane that is parallel to the disc space.

Therefore, in some embodiments, there is provided a method of preparing an intervertebral disc space between opposing vertebral endplates, comprising the steps of:

a) inserting a curved port into a lateral aspect of the disc space, the curved port having a bore.

Figure 20D:
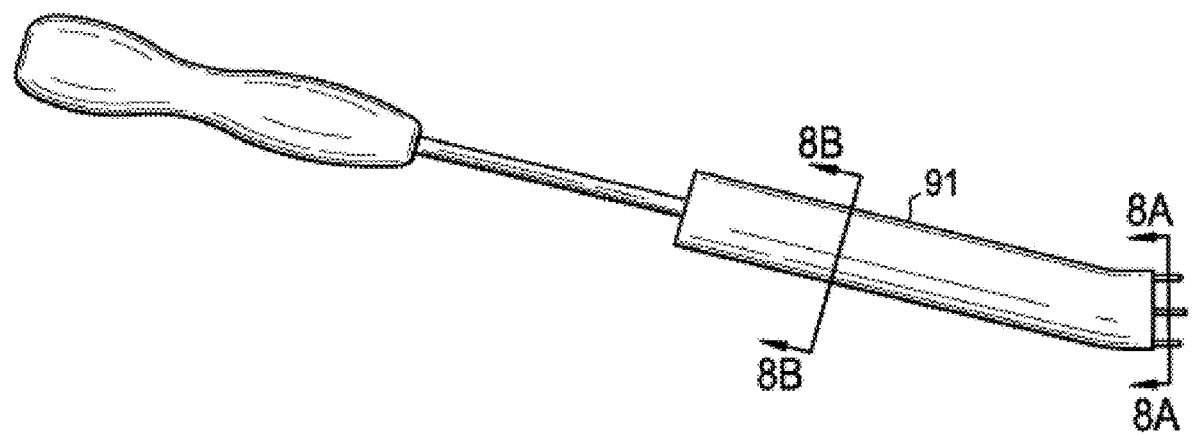
FIG. 20D discloses a handled port of the present invention.
Figure 21A:
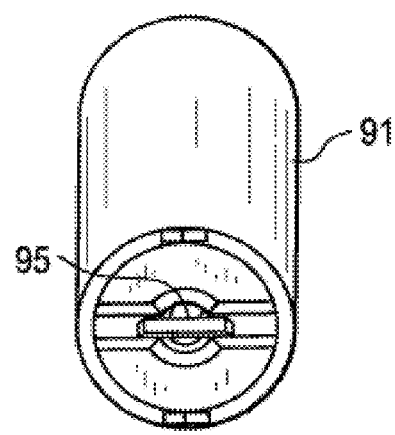
FIGS. 21A and 21B disclose cross-sectional views of the port of FIG. 20D.
Figure 21B:
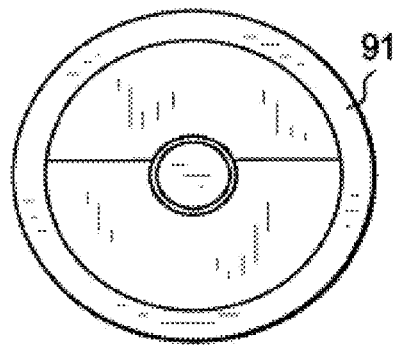

FIG. 20D discloses a port 91 and shaver 95 of the present invention. FIGS. 21A and 21B disclose cross-sectional views of the port-shaver assembly of FIG. 20D.

Preferably, the insertion is in a substantially coronal plane, as is generally the case for lateral implants. Preferably, the curved port has a substantially straight proximal end portion and a curved distal end portion. Preferably, the curved distal end portion of the curved port is docked to a vertebral body and is oriented substantially parallel to the opposing vertebral endplates in order to dictate endplate preparation that is parallel to the endplates. Preferably, the curved port has a distal end portion having a securement feature, through which docking of the port to a vertebral body occurs. This provides secure attachment of the port to a neighboring vertebral body.

In other embodiments, the method further comprises the steps of:

b) inserting a substantially straight, bendable shaver into the curved port;

c) advancing the shaver through the port and into an intervertebral disc space bounded by a vertebral endplate so that the shaver bends in the port, and d) contacting the shaver to the vertebral endplate. Preferably, the bore of the port has a shape corresponding to a cross-section of the shaver so as to determine the orientation of the shaver within the bore. Preferably, the bendable shaver has a shaft made of a flexible material, or has a shaft having a universal joint. Preferably, the target disc space is the L5/S1 or L4/L5 disc space. It is currently very problematic to access these two disc spaces with conventional lateral cage insertion techniques. Preferably, the curved port approaches the disc space during insertion from an upper end of the spine, as is the case with conventional lateral cage insertion techniques.

Now referring to FIGS. 22A through 22C, a catheter 101 with a steerable tip 103 is used to laterally access the caudal disc space. It is typically advanced through an incision in the skin of the patient and directed in a straight line towards the target disc. The steering mechanism in the catheter is then actuated to impart a curve in the tip of the catheter. This curve allows the surgeon to steer the tip directly towards the disc. The tip is then advanced until it contacts the target disc.

In some embodiments, a distal end portion 105 of the catheter includes a neuromonitoring sensor or electrode 141. This sensor connects to an external neuro-monitor as the catheter is advanced into the abdomen under fluoroscopic imaging. The function of this sensor is to detect the presence of nerves as the catheter tip is directed towards the target disc.

Once the tip is safely placed against a lateral portion of a disc, a guide wire 139 is advanced through the steerable tip and into the disc. In some embodiments, the electrode 141 can be a neuromonitoring band for sensing adjacent neural tissue. The function of this guide wire is to anchor the initial catheter in the disc and set the trajectory for the subsequent advance of dilation tubes.

In some embodiments, the steerable catheter and guidewire system is the VASCOCATH™, available from Polydiagnost of Pfaffenhofen, Germany.

Figure 23C:
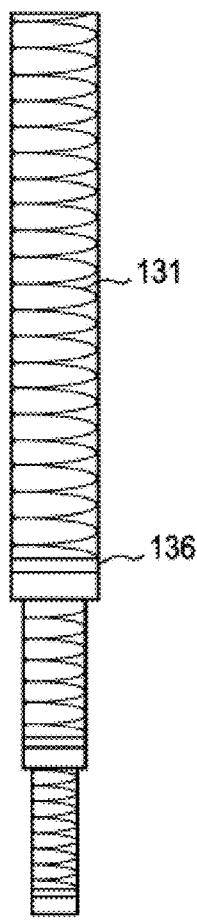
FIGS. 23C through 23E disclose telescoping dilation tubes.

Now referring to FIGS. 23A through 23C, the flexible dilation tubes 111, 113, 115 provide a minimally invasive access path for the subsequent advance of instruments or implants. Sequential flexible dilation tubes are advanced over the steerable catheter 101 and against the disc, thereby sequentially removing more and more tissue from the access path.

The flexible nature of these dilation tubes allows them to curve and thereby provide a parallel trajectory for instruments and implants laterally approaching the L4/L5 or L5/S1 disc spaces.

Therefore, and now referring to FIGS. 23A through 23C, in accordance with the present invention, there is provided an assembly for providing access to an intervertebral disc, comprising;

a) a catheter 101 having a steerable tip 103, b) a first flexible dilator tube 111 having a first bore 112 defining a first longitudinal axis, c) a second flexible dilator tube 113 having a second bore 114 defining a second longitudinal axis, wherein the first flexible dilator tube is received with the bore of the second flexible dilator tube, and wherein the steerable tip is received within the bore of the first flexible dilator tube.

Preferably, the steerable tip is curved, thereby imparting a curve upon the longitudinal axis of each of the first and second flexible dilator tubes. Preferably, each of the first and second dilator tubes has a proximal end portion and a distal end portion, and wherein the curve upon the longitudinal axis of each of the first and second flexible dilator tubes is located in the distal end portion of each tube.

In some embodiments, the catheter further comprises a guide wire.

In some embodiments, and now referring to FIGS. 23A through 23B, at least one of the flexible dilation tubes comprises a reinforcement member 131, preferably a fiber which is preferably metallic.

In some embodiments, each of the first and second flexible dilator tubes has a frustoconical distal end.

In accordance with the present invention, there is provided an assembly for providing access to an intervertebral disc, comprising;

d) a catheter having a steerable tip, e) a first flexible dilator tube having a first bore defining a first longitudinal axis, f) a second flexible dilator tube having a second bore defining a second longitudinal axis, wherein the first flexible dilator tube is received with the bore of the second flexible dilator tube, and wherein the steerable tip is received within the bore of the first flexible dilator tube.

In accordance with the present invention, there is provided a method of accessing a target intervertebral disc, comprising the steps of:

a) advancing a steerable catheter having a tip through an incision and towards the target disc, b) imparting a first curve in the tip of the steerable catheter, c) docking the curved tip upon the target disc, d) advancing a first flexible dilator tube over the curved tip to impart a first curve in the first flexible dilator tube.

Figure 23D:
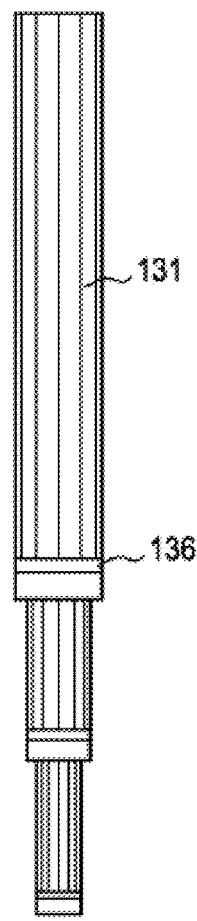
Figure 23E:
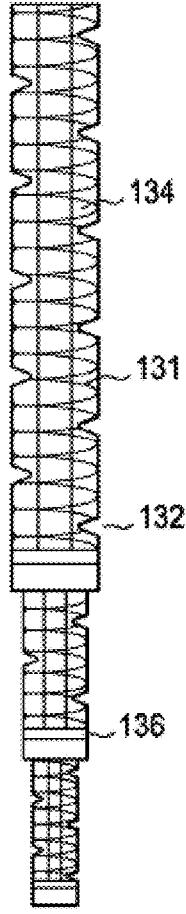

FIGS. 23C through 23E disclose telescoping dilation tubes. In FIG. 23C, each tube has helical reinforcement members 131 that are electrically connected to a neuromonitoring band 136. Thus, the ports may be used for neuromonitoring during approach. In FIG. 23D, each tube has vertical reinforcement members 131 that are electrically connected to a neuromonitoring band 136. In FIG. 23E, each tube has helical and vertical members 131 that are electrically connected to a neuromonitoring band 136. It also has slots 132 that provide additional flexibility.

Figure 24:
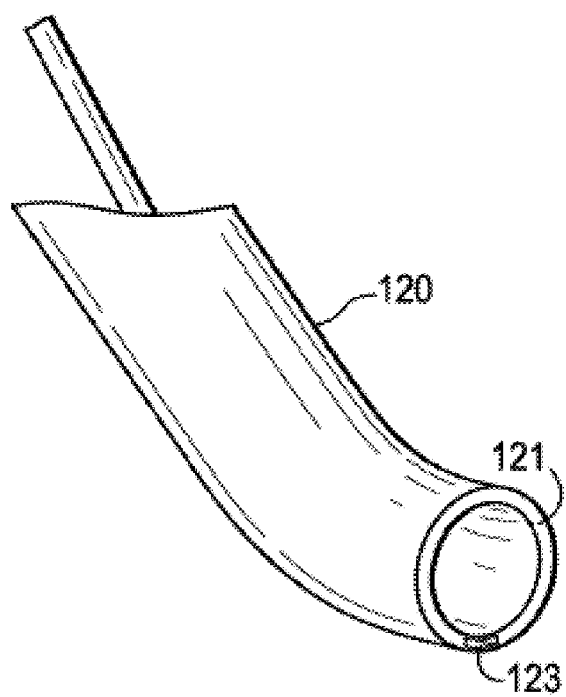
FIG. 24 discloses a flexible dilation tube with a bore for holding an endoscopic instrument.

Now referring to FIG. 24, the flexible dilation tubes comprise elastically deformable materials includes metallics and polymers. The flexible dilation tubes may further comprise axial reinforcing members (such as wires, fibers or struts) in order to provide improved column strength. The wall 121 of the flexible dilation tube 120 can have a secondary bore 123 to accept an endoscope for visualization of the disc and adjacent structures. Once dilation to the desired diameter is accomplished, the smaller dilation tubes may be removed. Inserts may be placed within the final dilation (or "port") in order to provide internal guiding surfaces for guiding instruments such as flexible shavers.

We claim:

1. A device for providing access to an intervertebral disc, comprising:
 a flexible tube having a proximal end portion, a distal end portion, a bore extending through the tube, and one or more interlaced metal fibers;
 wherein the tube is electrically connected to a neuromonitoring system, and
 wherein the metal fibers are electrically connected to the neuromonitoring system.

2. The device of claim 1, wherein the neuromonitoring system includes a neuromonitoring band to which the metal fibers are electrically connected.

3. The device of claim 1, wherein the metal fibers are longitudinally oriented with respect to the tube.

4. The device of claim 1, wherein the metal fibers are helically oriented with respect to the tube.

5. The device of claim 1, wherein the metal fibers reinforce the tube.

6. The device of claim 1, wherein the tube is curved along a length thereof.

7. The device of claim 1, wherein the tube is elastically-deformable.

8. The device of claim 1
 wherein the tube is expandable.

9. The device of claim 8, wherein the tube is telescopically-expandable.

10. The device of claim 1
 wherein the tube comprises a polymer.

11. The device of claim 1, wherein the tube has a frustoconical distal end.

12. The device of claim 1, wherein a wall of the tube has a bore with an endoscope disposed therein.

13. The device of claim 1, further comprising an instrument adapted to be inserted through the tube while the tube is curved.

* * * * *